(12) United States Patent
Choulika et al.

(10) Patent No.: US 7,098,031 B2
(45) Date of Patent: Aug. 29, 2006

(54) RANDOM INTEGRATION OF A POLYNUCLEOTIDE BY IN VIVO LINEARIZATION

(75) Inventors: Andre Choulika, Paris (FR); Jean-Stephane Joly, Versailles (FR); Violette Thermes, Paris (FR); Filomena Ristoratore, Ercolano (IT)

(73) Assignee: Cellectis SA, Paris (FR)

( * ) Notice: Subject to any disclaimer, the term of this patent is extended or adjusted under 35 U.S.C. 154(b) by 455 days.

(21) Appl. No.: 10/242,664

(22) Filed: Sep. 13, 2002

(65) Prior Publication Data

US 2003/0106077 A1    Jun. 5, 2003

Related U.S. Application Data

(60) Provisional application No. 60/330,639, filed on Oct. 26, 2001, provisional application No. 60/318,818, filed on Sep. 14, 2001.

(51) Int. Cl.
*C12N 15/63* (2006.01)
*C12N 15/00* (2006.01)

(52) U.S. Cl. .......................................... 435/455; 800/21
(58) Field of Classification Search ................ 435/455; 800/21, 25
See application file for complete search history.

(56) References Cited

U.S. PATENT DOCUMENTS 6,238,924 B1    5/2001    Dujon et al.

FOREIGN PATENT DOCUMENTS

WO        96 144 08        5/1996

OTHER PUBLICATIONS

1995 New England Biolabs Catalog, p. 82.*
Verma et al (Nature 389: 239-242, 1997).*
Anderson (Nature 392:25-30, 1998).*
Romano et al (Stem Cells 18: 19-39, 2000).*
Somia and Verma (Nature Reviews Genetics 1: 91-99, 2000).*
Wong, et al., "Genetic footprinting with mariner-based transpositio in *Pseudomonas aeruginosa*", PNAS, (Aug. 29, 2000), vol. 97, No. 18, 10191-10.
Cohen-Tannoudji, et al., "i-sCEi-Induced Gene Replacement at a Natural Locus in Embryonic Stem Cells", Molecular and Cellular Biology, (Mar. 1998), p. 144-1448.
Dijk, et al., "Tagging *Hansenula polymorpha* genes by random integration of linear DNA fragments (RALF)", Mol Genet Genomics, (2001) 266: 646-656.
Brown, et al., "Insertional mutagenesis of *Aspergillus fumigatus* ", Mol Gen Genet, (1998) 259: 327-335.
Maier, et al., "Mutagenesis via Insertional-or Restriction Enzyme-Mediated-Integration (REMI) as a Tool to Tag Pathogenicity Related Genes in Plant Pathogenic Fungi", Biol. Chem., (Jul./Aug. 1999) vol. 380, pp. 855-864.
Khoo, "Sperm-Mediated Gene Transfer Studies on Zebrafish in Singapore", Molecular Reproduction and Development, (2000), 56:278-280.
Thermes, et al., "*I-SceI* meganuclease mediates highly efficient transgenesis in fish", Mechanisms of Development 118 (2002) 91-98.

\* cited by examiner

*Primary Examiner*—Richard Schnizer
(74) *Attorney, Agent, or Firm*—Nixon & Vanderhye P.C.

(57)        ABSTRACT

The present invention concerns a method for in vivo generation of a linear polynucleotide with 5' and 3' free ends from a vector having no free end, said linear polynucleotide being integrated into the host cell genome. The vector having no free end according to the present invention comprise the polynucleotide to be linearized or excised flanked by a cleavage site, said cleavage site being preferably not found in the host cell genome. The present invention also relates to the resulting cells and their uses, for example for production of proteins or other genes, biomolecules, biomaterials, transgenic plants, vaccines, transgenic animals or for treatment or prophylaxis of a condition or disorder in an individual.

40 Claims, 14 Drawing Sheets

| Protein | | Organism | species | Size (AA) | Motif(AA) | Accession | Year | Authors | Journal |
|---|---|---|---|---|---|---|---|---|---|
| I-Ama I | Th. | Allomyces | macrogynus | 359 | | U02039 | 1994 | Paquin, B., Laforest, M.-J., Lang, BF. | PNAS 91: 11807-10 |
| I-Ani I | Th. | Aspergillus (Emericella) | nidulans | 319 | | | 1982 | Waring, R.B., Davies, R.W., Scazzocchio, C., Brown, T.A. | PNAS 79: 6332-36 |
| I-Bmo I | Exp | Bacillus | mojavensis | 266 | GIG | AF321518 | 2001 | Edgell, D.R., Shub, D.A. | PNAS 98: 7898-7903 |
| I-Ceu I | Exp | Chlamydomonas | eugametos | 218 | D | S15138 | 1991 | Gauthier, A., Turmel, M., Lemieux, C. | Curr Genet 19: 43-7 |
| I-Ceu II | Th. | Chlamydomonas | eugametos | 283 | D | | 1998 | Denovan-Wright, E.M., Nedelcu, A.M., Lee, R.W. | Plant Mol. Biol. 36: 285-95 |
| I-Chu I | Exp | Chlamydomonas | humicola | 218 | dd | L06107 | 1993 | Coté, V., Mercier, JP., Lemieux, C., Turmel, M. | Gene 129: 69-76 |
| I-Cmoe I | Pot | Chlamydomonas | moewusii | | HNH | | 2000 | Drouin, M., Lucas, P., Otis, C., Lemieux, C., Turmel, M. | NAR 28: 4566-72 |
| I-Cpa I | Pot | Chlamydomonas | pallidostigmatica | | | | 1995 | Turmel, M., Cote, V., Otis, C., Mercier, J.-P., Gray, M.W., Lonergan, K.M., Lemieux, C. | Mol. Biol. Evol. 12: 533-45 |
| I-Cpa II | Pot | Chlamydomonas | pallidostigmatica | | | | 1995 | Turmel, M., Mercier, J.-P., Cote, V., Otis, C., Lemieux, C. | NAR 23: 2519-25 |
| I-Cre I | Exp | Chlamydomonas | reinhardtii | 163 | D | X01977 | 1985 | Rochaix, JD., Rahire, M., Michel, F. | NAR 13: 975-84 |
| I-Cre II | Pot | Chlamydomonas | reinhardtii | | | | 1999 | Holloway, S.P., Deshpande, N.N., Herrin, D.L. | Curr. Genet. 36: 69-78 |
| I-Cre V | Pot | Chlamydomonas | reinhardtii | | HNH | | 1999 | Holloway, S.P., Deshpande, N.N., Herrin, D.L. | Curr. Genet. 36: 69-78 |
| I-Csm I | Exp | Chlamydomonas | smithii | 237 | dd | X55305 | 1990 | Colleaux, L., Michel-Wolwertz, M-R., Matagne, RF., Dujon, B. | Mol Gen Genet 223: 288-296 |
| I-Cvu I | Pot | Chlorella | vulgaris | | | | 1998 | Watanabe, K.I., Ehara, M., Inagaki, Y., Ohama, T. | Gene 213: 1-7 |
| I-Ddi I | Pot | Dictyostelium | discoideum | | | | 1997 | Ogawa, S., Naito, K., Angata, K., Morio, T., Urushihara, H., Tanaka, Y. | Gene 191: 115-21 |
| I-Ddi II | Pot | Dictyostelium | discoideum | | | | 1997 | Yoshino, R., Morio, T., Tanaka, Y. | Unpublished observations |
| I-Dir I | Exp | Didymium | iridis | 244 | - | X71792 | 1993 | Johansen, S., Embley, TM., Willassen, N.P. | NAR 21: 4405 |
| I-Dmo I | Exp | Desulfurococcus | mobilis | 194 | DD | P21505 | 1985 | Kjems, J., Garrett, R.A. | Nature 318: 675-77 |

Figure 2A

| Protein | | Organism | species | Size (AA) | Motif(AA) | Accession | Year | Authors | Journal |
|---|---|---|---|---|---|---|---|---|---|
| I-Hmu I | Exp | Bacteriophage | SPO1 | 174 | - | M37686 | 1990 | Goodrich-Blair, H., Scarlato, V., Gott, JM., Xu, MQ., Shub, DA. | Cell 63: 417-424 |
| I-Hmu II | Exp | Bacteriophage | SP82 | 187 | - | | 1993 | Lambowitz, A.M., Belfort, M. | Annu Rev Biochem 62: 587-622 |
| I-Hsp I | Pot | Halobacterium | sp. | | | | 1998 | Ng, W.V., Ciufo, S.A., Smith, T.M., Bumgarner, R.E., Baskin, D., Faust, J., Hall, B., Loretz, C., Seto, J., Slagel, J., Hood, L., DasSarma, S. | Genome Res. 8: 1131-41 |
| I-Lla I | Pot | Lactococcus | lactis | | | | 2001 | internet address: rebase.neb.com/rebase/rebase.ho ming.html | |
| I-Naa I | Pot | Naegleria | andersoni | | | | 1992 | Embley, TM., Dyal, P., Kilvington, S. | NAR 20: 6411 |
| I-Nan I | Pot | Naegleria | andersoni | | | | 1994 | De Jonckheere, J.F. | J. Eukaryot. Microbiol. 41: 457-63 |
| I-Ncl I | Pot | Naegleria | gruberi | | | | 2001 | internet address: rebase.neb.com/rebase/rebase.ho ming.html | |
| I-Ncr I | Exp | Neurospora | crassa | 304 | GIG | S06367 | 1988 | Mota, EM., Collins, R.A. | Nature 332: 654-656 |
| I-Ncr II | Th. | Neurospora | crassa | 317 | GIG | X06884 | 1988 | Collins et al. | Nucleic Acids Res 16: 1125-34 |
| I-Ngr I | Pot | Naegleria | gruberi | | | | 2001 | internet address: rebase.neb.com/rebase/rebase.ho ming.html | |
| I-Nit I | Pot | Naegleria | italica | | | | 2001 | internet address: rebase.neb.com/rebase/rebase.ho ming.html | |
| I-Nja I | Pot | Naegleria | jamiesoni | | | | 2001 | internet address: rebase.neb.com/rebase/rebase.ho ming.html | |
| I-Nsp I | Pot | Naegleria | sp. | | | | 2001 | internet address: rebase.neb.com/rebase/rebase.ho ming.html | |
| I-Pan I | Th. | Podospora | anserina | 243 | dd | X55026 | 1985 | Cummings, DJ., MacNeil, IA., Domenico, J., Matsuura, ET. | J Mol Biol 185: 659-80 |
| I-Pbo I | Pot | Protosiphon | botryoides | | | | 1998 | Watanabe, K.I., Ehara, M., Inagaki, Y., Ohama, T. | Gene 213: 1-7 |

Figure 2B

| Protein | | Organism | species | Size (AA) | Motif(AA) | Accession | Year | Authors | Journal |
|---|---|---|---|---|---|---|---|---|---|
| I-Pcu I | Pot | Peperomia | cubensis | | | | 2001 | internet address: rebase.neb.com/rebase/rebase.homing.html | |
| I-PcuA I | Pot | Peperomia | cubensis | | | | 2001 | internet address: rebase.neb.com/rebase/rebase.homing.html | |
| I-PcuV I | Pot | Peperomia | cubensis | | | | 2001 | internet address: rebase.neb.com/rebase/rebase.homing.html | |
| I-Pgr I | Pot | Peperomia | griseoargentea | | | | 2001 | internet address: rebase.neb.com/rebase/rebase.homing.html | |
| I-Pob I | Pot | Peperomia | obtusifolia | | | | 2001 | internet address: rebase.neb.com/rebase/rebase.homing.html | |
| I-Por I | Pot | Pyrobaculum | organotrophum | | | | 2001 | internet address: rebase.neb.com/rebase/rebase.homing.html | |
| I-Por II | Pot | Pyrobaculum | organotrophum | | | | 2001 | internet address: rebase.neb.com/rebase/rebase.homing.html | |
| I-Ppb I | Pot | Peperomia | polybotrya | | | | 2001 | internet address: rebase.neb.com/rebase/rebase.homing.html | |
| I-Ppo I | Exp | Physarum | polycephalum | 185 | - | M38131 | 1990 | Muscarella, DE., Ellison, EL., Ruoff, BM., Vogt, VM. | Mol Cell Biol 10: 3386-96 |
| I-Sca I | Th. | Saccharomyces | capensis | 250 | DD | X95974 | 2000 | Monteilhet, C., Dziadkowiec, D., Szczepanek, T., Lazowska, J. | Nucleic Acids Res. 28: 1245-1251 |
| I-Sce I | Exp | Saccharomyces | cerevisiae | 235 | dd | P03882 | 1985 | Jacquier & Dujon | |
| I-Sce II | Exp | Saccharomyces | cerevisiae | 316 | DD | P03878 | 1980 | Bonitz, S. G., Coruzzi, G., Thalenfeld, B. E., Tzagoloff, A., Macino, G. | J Biol Chem 255: 11927-41 |
| I-Sce III | Exp | Saccharomyces | cerevisiae | 335 | DD | P03877 | 1980 | Bonitz, S. G., Coruzzi, G., Thalenfeld, B. E., Tzagoloff, A., Macino, G. | J Biol Chem 255: 11927-41 |
| I-Sce IV | Exp | Saccharomyces | cerevisiae | 307 | dd | - | 1992 | Séraphin et al. | Gene 113: 1-8 |
| I-Sex I | Pot | Saccharomyces | exiguus | | | | 2001 | internet address: rebase.neb.com/rebase/rebase.homing.html | |

Figure 2C

| Protein | | Organism | species | Size (AA) | Motif(AA) | Accession | Year | Authors | Journal |
|---|---|---|---|---|---|---|---|---|---|
| I-Sne I | Pot | Simkania | negevensis | | | | 2001 | internet address: rebase.neb.com/rebase/rebase.ho ming.html | |
| I-Spo I | Pot | Schizosaccharomyces | pombe | | | | 2001 | internet address: rebase.neb.com/rebase/rebase.ho ming.html | |
| I-SPβ I | Pot | Bacteriophage | SPβ | | | | 1998 | Lazarevic, V., Soldo, B., Dusterhoft, A., Hilbert, H., Mauel, C., Karamata, D. | PNAS 95: 1692-97 |
| I-Squ I | Pot | Scenedesmus | quadricauda | | | | 2001 | internet address: rebase.neb.com/rebase/rebase.ho ming.html | |
| I-Tde I | Pot | Torulaspora | delbrueckii | | | | 2001 | internet address: rebase.neb.com/rebase/rebase.ho ming.html | |
| I-Tev I | Exp | Bacteriophage | T4 | 245 | GIG | M12742 | 1989 | West et al. | J Biol Chem 264: 10343-10346 |
| I-Tev II | Exp | Bacteriophage | T4 | 258 | GIG | | 1987 | Shub et al. | Cold Spring H. Symp Quant Biol: 193-200 |
| I-Tev III | Exp | Bacteriophage | RB3 | 269 | | X59078 | 1991 | Eddy, S.R., Gold, L. | Genes Dev 5: 1032-1041 |
| I-Uar A | Pot | archaeon | Uncultured | | | AB027540 | 2001 | internet address: rebase.neb.com/rebase/rebase.ho ming.html | |
| I-Vin I | Pot | Venturia | inaequalis | | | | 2001 | internet address: rebase.neb.com/rebase/rebase.ho ming.html | |
| I-Zbi I | Pot | Zygosaccharomyces | bisporus | | | | 2001 | internet address: rebase.neb.com/rebase/rebase.ho ming.html | |
| F-Sce I | Exp | Saccharomyces | cerevisiæ | 476 | DD | M63839 | 1991 | Nakagawa et al. | J. Biol. Chem. 266: 1977-1984 |
| F-Sce II | Exp | Saccharomyces | cerevisiæ | 586 | DD | M14678 | 1983 | Kostriken, R., JN. Strathern, AJS. Klar, JB. Hicks, F. Heffron | Cell 35: 167-174 |
| F-Tev I | Exp | Bacteriophage | T4 | 221 | | | 1994 | Sharma, M., Hinton, D.M. | J. Bacteriol. 176: 6439-6448 |
| F-Tev II | Th. | Bacteriophage | T4 | 205 | | | 1997 | Kadyrov, F.A., Shlyapnikov, M.G., Kryukov, V.M. | FEBS Lett. 415: 75-80 |
| PI-Aae I | Th. | Aquifex | aeolicus | 347 | DD | | 1998 | Deckert, G. et al. | Nature 392 (6674), |

Figure 2D

| Protein | | Organism | species | Size (AA) | Motif(AA) | Accession | Year | Authors | Journal |
|---|---|---|---|---|---|---|---|---|---|
| PI-Ape I | Th. | Aeropyrum | pernix | 468 | DD | B72665 | 1999 | Kawarabayasi,Y, et al | DNA Res. 6 (2), 83-101 |
| PI-APSE I | Th. | Bacteriophage | Acyrthosiphon pisum | 306 | - | | 2001 | internet address: bioinformatics.weizmann.ac.il/~pietro/inteins | |
| PI-Bsp I | Th. | Bacteriophage | prophage A | 385 | DD | | 2001 | internet address: bioinformatics.weizmann.ac.il/~pietro/inteins | |
| PI-Ceu I | Exp | Chlamydomonas | eugametos | 457 | DD | | 2001 | internet address: bioinformatics.weizmann.ac.il/~pietro/inteins | |
| PI-Cir I | Th. | Chilo | iridescent | 339 | DD | | 2001 | internet address: bioinformatics.weizmann.ac.il/~pietro/inteins | |
| PI-Cry I | Th. | Filobasidiella (Cryptococcus) | neoformans | 172 | - | | 2001 | internet address: bioinformatics.weizmann.ac.il/~pietro/inteins | |
| PI-Ctr I | Exp | Candida | tropicalis | 471 | DD | M64984 | 1993 | Gu, HH., Xu, J., Gallagher, M., Dean, GE. | J Biol Chem 268: 7372-81 |
| PI-Dra I | Th. | Deinococcus | radiodurans | 367 | DD | | 2001 | internet address: bioinformatics.weizmann.ac.il/~pietro/inteins | |
| PI-Gth I | Th. | Guillardia | theta | 160 | - | | 2001 | internet address: bioinformatics.weizmann.ac.il/~pietro/inteins | |
| PI-Hsp I | Th. | Halobacterium | sp. | 183 | - | | 2001 | internet address: bioinformatics.weizmann.ac.il/~pietro/inteins | |
| PI-Mav I | Exp | Mycobacterium | avium | 337 | DD | | 2001 | internet address: bioinformatics.weizmann.ac.il/~pietro/inteins | |
| PI-Mch I | Th. | Mycobacterium | chitae | 365 | - | | 2001 | internet address: bioinformatics.weizmann.ac.il/~pietro/inteins | |
| PI-Meth I | Exp | Methanobacterium | thermoautotrophicum | 134 | - | | 2001 | internet address: bioinformatics.weizmann.ac.il/~pietro/inteins | |
| PI-Mfa I | Th. | Mycobacterium | fallax | 364 | DD | | 2001 | internet address: bioinformatics.weizmann.ac.il/~pietro/inteins | |

Figure 2E

| Protein | | Organism | species | Size (AA) | Motif(AA) | Accession | Year | Authors | Journal |
|---|---|---|---|---|---|---|---|---|---|
| PI-Mfl I | Exp | Mycobacterium | flavescens | 421 | DD | | 2001 | internet address: bioinformatics.weizmann.ac.il/~piet ro/inteins | |
| PI-Mfl II | Exp | Mycobacterium | flavescens | 364 | DD | | 2001 | internet address: bioinformatics.weizmann.ac.il/~piet ro/inteins | |
| PI-Mfl II 144 | Th. | Mycobacterium | flavescens | 365 | DD | | 2001 | internet address: bioinformatics.weizmann.ac.il/~piet ro/inteins | |
| PI-Mga I | Th. | Mycobacterium | gastri | 420 | DD | | 2001 | internet address: bioinformatics.weizmann.ac.il/~piet ro/inteins | |
| PI-Mga III | Th. | Mycobacterium | gastri | 369 | DD | | 2001 | internet address: bioinformatics.weizmann.ac.il/~piet ro/inteins | |
| PI-Mgo I | Th. | Mycobacterium | gordonae | 420 | DD | | 2001 | internet address: bioinformatics.weizmann.ac.il/~piet ro/inteins | |
| PI-Min I | Th. | Mycobacterium | intracellulare | 335 | DD | | 2001 | internet address: bioinformatics.weizmann.ac.il/~piet ro/inteins | |
| PI-Mja I | Th. | Methanococcus | jannaschii | 500 | DD | | 2001 | internet address: bioinformatics.weizmann.ac.il/~piet ro/inteins | |
| PI-Mja V | Exp | Methanococcus | jannaschii | 169 | - | | 2001 | internet address: bioinformatics.weizmann.ac.il/~piet ro/inteins | |
| PI-Mka I | Th. | Mycobacterium | kansasii | 420 | DD | | 2001 | internet address: bioinformatics.weizmann.ac.il/~piet ro/inteins | |
| PI-Mle I | Exp | Mycobacterium | leprae | 365 (366) | Dd | X73822 | 1994 | Davis EO, Thangaraj HS, Brooks PC, Colston MJ. | EMBO J. Feb 1;13(3):699-703. |
| PI-Mma I | Th. | Mycobacterium | malmoense | 420 | DD | | 2001 | internet address: bioinformatics.weizmann.ac.il/~piet ro/inteins | |
| PI-Msh I | Th. | Mycobacterium | shimoidei | 365 | DD | | 2001 | internet address: bioinformatics.weizmann.ac.il/~piet ro/inteins | |
| PI-Msm I | Th. | Mycobacterium | smegmatis | 140 | - | | 2001 | internet address: bioinformatics.weizmann.ac.il/~piet ro/inteins | |

Figure 2F

| Protein | | Organism | species | Size (AA) | Motif(AA) | Accession | Year | Authors | Journal |
|---|---|---|---|---|---|---|---|---|---|
| PI-Msm II | Th. | Mycobacterium | smegmatis | 426 | DD | | 2001 | internet address: bioinformatics.weizmann.ac.il/~piet ro/inteins | |
| PI-Mth I | Th. | Mycobacterium | thermoresistibile | 366 | DD | | 2001 | internet address: bioinformatics.weizmann.ac.il/~piet ro/inteins | |
| PI-Mtu | Exp | Mycobacterium | tuberculosis | 441 | DD | | 2001 | internet address: bioinformatics.weizmann.ac.il/~piet ro/inteins | |
| PI-Mtu I | Exp | Mycobacterium | tuberculosis | 439 (441) | DD | X58485 | 1992 | Davis EO, Jenner PJ, Brooks PC, Colston MJ, Sedgwick SG. | Cell Oct 16;71(2):201-10 |
| PI-MtuH I | Exp | Mycobacterium | tuberculosis | 415 | DD | | 2001 | internet address: rebase.neb.com/rebase/rebase.ho ming.html | |
| PI-Mxe I | Exp | Mycobacterium | xenopi | 198 | - | | 2001 | internet address: bioinformatics.weizmann.ac.il/~piet ro/inteins | |
| PI-Pab I | Th. | Pyrococcus | abyssi | 164 | - | | 2001 | internet address: bioinformatics.weizmann.ac.il/~piet ro/inteins | |
| PI-Pab III | Th. | Pyrococcus | abyssi | 394 | DD | | 2001 | internet address: bioinformatics.weizmann.ac.il/~piet ro/inteins | |
| PI-Pfu I | Exp | Pyrococcus | furiosus | 454 | | | 1999 | Komori, K., Fujita, N., Ichiyanagi, K., Shinagawa, H., Morikawa, K., Ishino, Y. | NAR 27: 4167-74 |
| PI-Pfu II | Exp | Pyrococcus | furiosus | 525 | DD | | 1999 | Komori, K., Fujita, N., Ichiyanagi, K., Shinagawa, H., Morikawa, K., Ishino, Y. | NAR 27: 4167-74 |
| PI-Pho I | Th. | Pyrococcus | horikoshii | 167 | - | | 2001 | internet address: bioinformatics.weizmann.ac.il/~piet ro/inteins | |
| PI-Pho II | Th. | Pyrococcus | horikoshii | 377 | DD | | 2001 | internet address: bioinformatics.weizmann.ac.il/~piet ro/inteins | |
| PI-Pko | Exp | Pyrococcus | kodakaraensis | 360 | DD | | 1997 | Takagi, M., Nishioka, M., Kakihara, H., Kitabayashi, M., Inoue, H., Kawakami, B., Oka, M., Imanaka, T. | Appl. Environ. Microbiol. 63: 4504-10 |

Figure 2G

| Protein | | Organism | species | Size (AA) | Motif(AA) | Accession | Year | Authors | Journal |
|---|---|---|---|---|---|---|---|---|---|
| PI-PkoII | Th. | Pyrococcus | kodakaraensis | 537 | DD | | 1997 | Takagi, M., Nishioka, M., Kakihara, H., Kitabayashi, M., Inoue, H., Kawakami, B., Oka, M., Imanaka, T. | Appl. Environ. Microbiol. 63: 4504-10 |
| PI-PpuI | Th. | Porphyra | purpurea | 150 | - | | 2001 | internet address: bioinformatics.weizmann.ac.il/~piet ro/inteins | |
| PI-PspI | Exp | Pyrococcus | sp. | 537 | DD | | 1993 | Xu, M.-Q., Southworth, MW., Mersha, FB., Hornstra, LJ., Perler, FB. | Cell 75: 1371-77 |
| PI-RmaI | Exp | Rhodothermus | marinus | 428 | DD | | 1997 | Liu, X.-Q., Hu, Z. | PNAS 94: 7851-56 |
| PI-SceI | Exp | Saccharomyces | cerevisiae | 454 | DD | M21609 | 1990 | Hirata, R. et al. | J Biol Chem 265: 6726-6733 |
| PI-SPβI | Th. | Bacteriophage | SPβ | 385 | DD | | 1998 | Lazarevic, V., Soldo, B., Dusterhoft, A., Hilbert, H., Mauel, C., Karamata, D. | PNAS 95: 1692-97 |
| PI-SspI | Exp | Synechocystis | sp. | 429 | DD | | 2001 | internet address: bioinformatics.weizmann.ac.il/~piet ro/inteins | |
| PI-SspIII | Th. | Synechocystis | sp. | 123 +36 | - | | 2001 | internet address: bioinformatics.weizmann.ac.il/~piet ro/inteins | |
| PI-SspIV | Th. | Synechocystis | sp. | 436 | HNH | | 2001 | internet address: bioinformatics.weizmann.ac.il/~piet ro/inteins | |
| PI-TacI | Th. | Thermoplasma | acidophilum | 173 | - | | 2001 | internet address: bioinformatics.weizmann.ac.il/~piet ro/inteins | |
| PI-TagI | Exp | Thermococcus | aggregans | 360 | DD | | 2001 | internet address: bioinformatics.weizmann.ac.il/~piet ro/inteins | |
| PI-TagII | Exp | Thermococcus | aggregans | 538 | DD | | 2001 | internet address: bioinformatics.weizmann.ac.il/~piet ro/inteins | |
| PI-TfuI | Exp | Thermococcus | fumicolans | 360 | DD | | 2000 | Saves, I., Ozanne, V., Dietrich, J., Masson, J.M. | JBC 275: 2335-41 |
| PI-TfuII | Exp | Thermococcus | fumicolans | 389 | DD | | 2000 | Saves, I., Ozanne, V., Dietrich, J., Masson, J.M. | JBC 275: 2335-41 |
| PI-ThyII | Exp | Thermococcus | hydrothermalis | 538 | DD | | 2001 | internet address: bioinformatics.weizmann.ac.il/~piet ro/inteins | |

Figure 2H

| Protein | | Organism | species | Size (AA) | Motif(AA) | Accession | Year | Authors | Journal |
|---|---|---|---|---|---|---|---|---|---|
| PI-Thy III | Exp | Thermococcus | hydrothermalis | 390 | DD | | 2001 | internet address: bioinformatics.weizmann.ac.il/~piet ro/inteins | |
| PI-Tli I | Exp | Thermococcus | litoralis | 390 | DD | M74198 | 1992 | Perler et al. | PNAS 89: 5577-5581 |
| PI-Tli II | Exp | Thermococcus | litoralis | 541 | DD | M74198 | 1993 | Lambowitz, A.M., Belfort, M. | Annu Rev Biochem 62: 587-622 |
| PI-Tsp II | Exp | Thermococcus | sp. | 536 | DD | | 2001 | internet address: bioinformatics.weizmann.ac.il/~piet ro/inteins | |
| PI-Tsp III | Exp | Thermococcus | sp. | 390 | DD | | 2001 | internet address: bioinformatics.weizmann.ac.il/~piet ro/inteins | |
| PI-Tvo I | Th. | Thermoplasma | volcanium | 186 | - | | 2001 | internet address: bioinformatics.weizmann.ac.il/~piet ro/inteins | |

Figure 2I

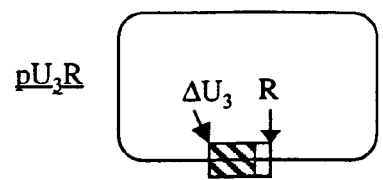
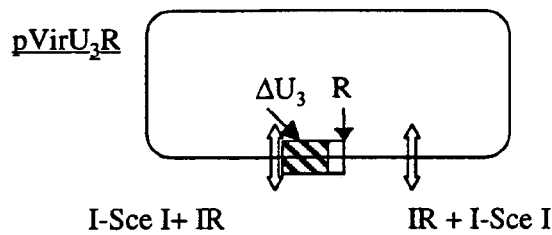
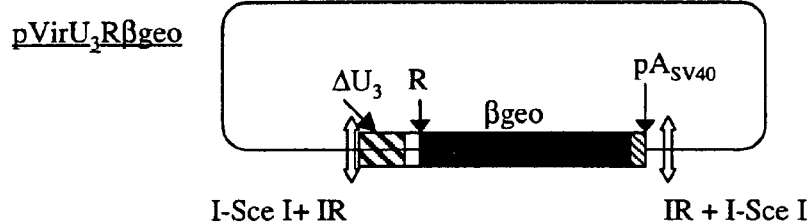
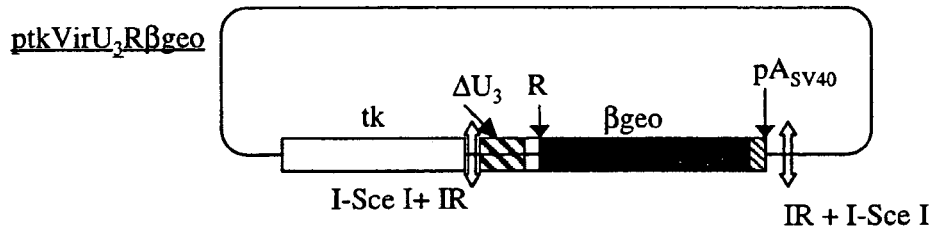
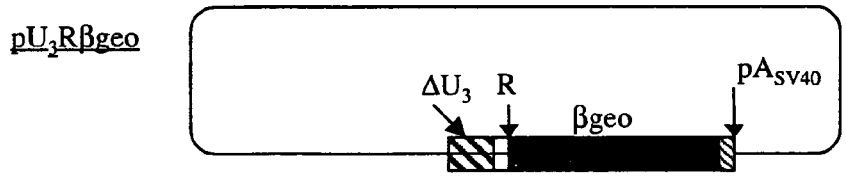
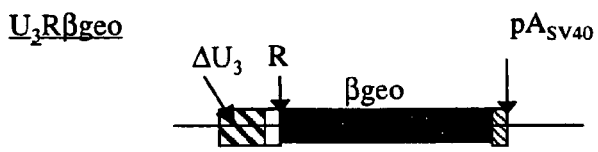
FIGURE 4

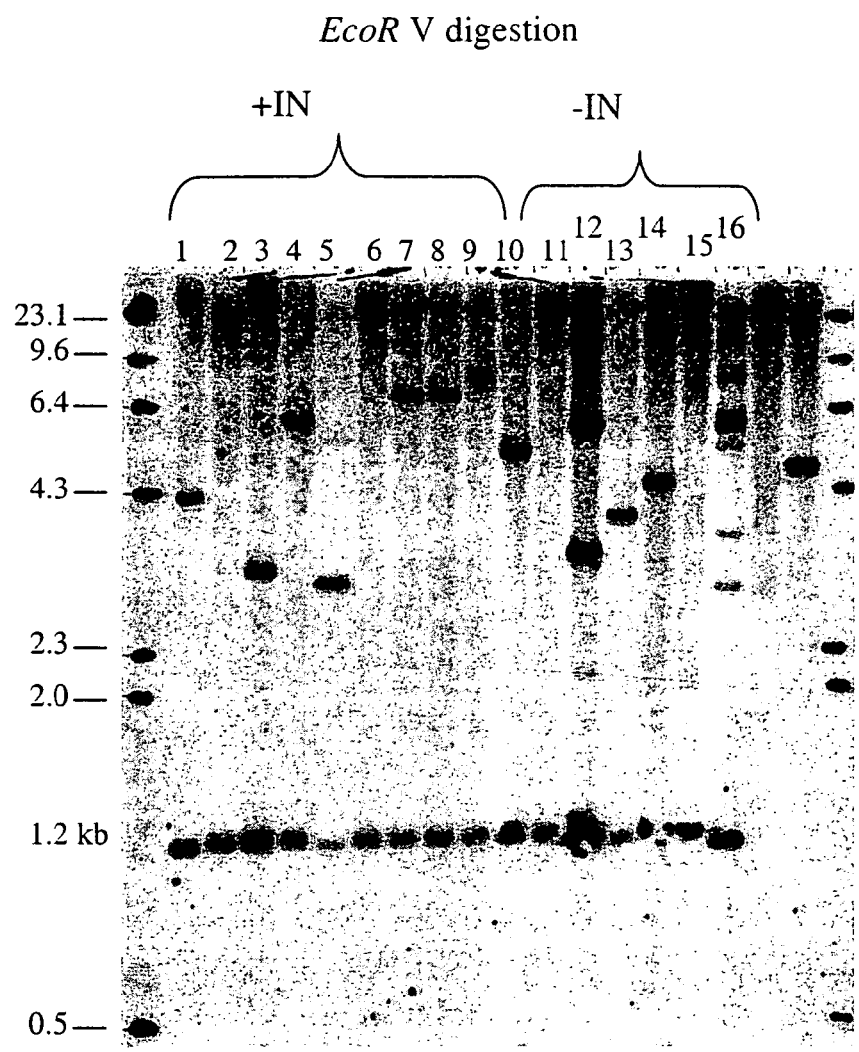
FIGURE 6

RANDOM INTEGRATION OF A POLYNUCLEOTIDE BY IN VIVO LINEARIZATION

This application claims the benefit of Provisional Application No. 60/318,818, filed 14 Sep. 2001, and 60/330,639, filed 26 Oct. 2001 the entire content of which is hereby incorporated by reference in this application.

BACKGROUND

1. Field of the Invention

The invention concerns a process of in vivo liberation a linear DNA fragment from a vector in order to integrate this fragment into the cellular genome. The invention further concerns the use of this process and the results of this use.

2. Brief Description of the Prior Art

The first breakthrough of reverse genetics 20 years ago was Transgenesis. The transgenesis is the technique which allows to introduce a exogenous DNA sequence into a host cell. For example, DNA micro-injection in an egg fertilized by mammal leads, in a certain number of cases, to the integration of micro-injected DNA molecule into the genome of the fertilized egg. Transgenesis implies that a foreign DNA fragment is introduced into the genome of a multicellular organism and transmitted to progeny. Therefore, the foreign DNA must be present in a stable form in the embryo at an early stage of development in order to be transmitted into progeny.

DNA transfection in mammal cells by means of precipitated calcium phosphate precipitation can also lead, in a certain number of cases, to the integration of the exogneous DNA to the genome of the cell host which is called stable transfection. The exogenous DNA can be introduced into cells under two forms, either linear or circular. When the DNA is introduced under linear form, the linear fragment is prepared in vitro before its introduction into the host cell, generally by excision of the desired fragment with restriction enzyme from a plasmid for example. As regards the DNA under circular form, the introduced DNA is generally a supercoiled plasmid.

All cells have systems of maintenance and repair of their DNA. One of the particular signals of stress which activates the intervention of these systems is the generation of DNA free ends in the cell. The cell has then two solutions to resolve this type of problem:

The first solution is the degradation of the DNA presenting the free ends (for example the case where the cell should eliminate a DNA being able to have a viral activity). This solution is based on the presence in these systems of maintenance and repair of exonucleases, which degrade the DNA by digesting it from the free ends.

An other solution is the recombination of the free ends with the cellular genome. This recombination can take different forms, notably the integration of the exogenous molecule into the genome of the cell.

As a consequence, the works aiming at integrating of the exogenous DNA by introduction of naked double-stranded DNA under circular or linear form meet three types of major problems as well as certain number of collateral problems.

The first one of these problems is the efficiency of the integration of the exogenous molecule in the DNA of the cell host. This lack of efficiency implies the injection of very hight amount of exogenous DNA for a very few number of integration. In some species such as fish, plants or insects, the exonucleases are so efficient that the exogenous DNA is never integrated in the chromosome and it stays episomal. For example, if the circular form is used for the exogenous DNA, a nick is necessary for having integration. Indeed, the integration process needs the presence of a free end. If the linear form is used, most of the exogenous DNA is degraded by the exonucleases due to the presence of the free ends.

The second problem is the integrity of the integrated DNA. The linear fragment of exogenous DNA exposes its free ends to the cellular exonucleases before its arrival to the nucleus. This prolonged exhibition of its ends in the cell limits in a significant way the chances of the exogenous DNA to be wholly integrated into the cellular genome. A way of increasing the chances to be wholly integrated into the genome consists in adding some cohesive single-stranded DNA overhangs at each ends of the exogenous DNA, for example made by digestion with the same restriction enzyme. These cohesive extremities allow the DNA fragments to associate in a multimer and to prevent the complete degradation of the DNA before its integration. Another way of increasing the chances is to surround the DNA fragment to integrate with long and neutral DNA sequences. In the case of the exogenous DNA is included in a supercoiled plasmid, the intregrated fragment comprises not only the exogenous DNA but also the whole vector.

The third problem is the control of the number of integrated copies. The multimerization, deliberated or not, of the exogenous DNA presents the inconvenience to favor the insertion of several copies of the exogenous DNA fragment. Similarly, when the exogenous DNA has a circular form, the plasmid is integrated as a concatemer. This multiple insertion has for consequence to introduce a chromosome instability and to result in problems of regulation of the expression due to the presence of the same gene in multiple copies.

Transgenesis is, more than ever, an essential tool for biologists. The study of human diseases relies to a great extent on the use of animal models. Vast gene sequence informations are available for the pharmaceutical industry. These informations would provide new targets for drug. However, the function of the majority of the genes and related proteins in an organism remains unknown and the efficiency of target validation does not appear to have significantly changed.

Genetic studies and structural genomics have shown that biochemical pathways and physiology are highly conserved throughout the animal world. Animal models can therefore be used to investigate processes relevant to human diseases. Animal model can be used to efficiently identify and validate optimal screening targets. Screening target selection can be improved and will lead to fewer failures and a more efficient drug development process.

Mouse is a well known mammalian model which is abundantly used. The most widely used method for the production of transgenic animals is the microinjection of DNA into the pronuclei of fertilized embryos. This method is rather efficient for the production of transgenic mice but is much less efficient for the production of large transgenic mammals such as cows and sheep. Moreover, the transgenic animals from the available transgenesis method are often mosaic for the transgene resulting in the lack of transmission of the transgene to the progeny. Some animals present a high resistance to transgenesis such as fish or bird. Among them, the problem of fish transgenesis is more detailed below.

Tank fish have risen to high popularity as vertebrate models in developmental biology and genetics. Indeed, the zebrafish (Danio rerio) is a popular model system for vertebrate developmental studies because it offers the opportunity to combine classical genetic analysis with an easily accessible and manupilable embryo. Genetic studies of the zebrafish benefit from the 2–3 month generation time, the ability of females to routinely lay hundreds of egg, and the small size of the adults. Embryological studies benefit from the large, transparent embryos.

However, the usefulness of tank fish is still limited by the lack of some methodological tools, above all a simple and efficient technology for transgenesis, which has become a major technique in fundamental research and has varied applications in agronomy and biomedecine. In particular, attempts to establish embryonic stem (ES) cells in fish as cellular vectors for transgenesis, have so far been unsuccessful.

Therefore, the method of choice to generate transgenic fish remains the injection of high concentrations of DNA (approximately $10^6$ plasmid copies) in the cytoplasm of one cell-stage embryos. Plasmids have been microinjected in linearized and circular form, and in both types of experiments transgenesis has been achieved. This technology is fast and easy, due to the transparency and great size of most fish eggs, but unfortunately, it is also rather inefficient, with a frequency of genomic integration and germline transmission which usually lies in a range of a few percents [Stuart et al., 1988 *Development* 103, 403–412; Stuart et al., 1990, *Development* 109, 577–584; Culp et al., 1991, *Proc Natl Acad Sci USA*, 88, 7953–57; Lin et al., 1994 *Dvelopmental biology* 161, 77–83; Collas et al., 1998 *Transgenic Research*, 7, 303–309]. Recent studies have shown that this is likely to be due to late and mosaic integrations: DNA persists in an unintegrated form in the egg cytoplasm and is inherited only by a subset of blastomeres. After injection, the plasmid sequences are transiently amplified and form long concatemers consisting of many unit-length copies of the plasmid arranged in tandem (Stuart et al. 1988, supra). The foreign DNA usually inserts into one site in the host genome but usually consists of tandem arrays of the original injected construct (Culp et al., 1991, Supra).

It is generally accepted that increasing the frequency of transgenic fish generated by plasmid microinjection is difficult. Injecting higher amounts of DNA is toxic to the embryos so one must attempt to improve the efficiency of integration. Several attempts to improve the rate of integration and transmission of transgenes have been performed. For example, the use of DNA-NLS complexes has been reported, although most authors found no improvements with this technology [Liang et al., 2000 *Mol Reprod Dev* 55, 8–13]. In principle, technologies using flanking repeats of adeno-associated virus [Fu, 1998 *Nature Biotech*, 16, 253–257] or of transposons [Izsvak et al., 2000 *J Mol Biol* 302, 93–102] may also increase transgene integration. However, to the best knowledge of the inventors, positive results have not been not reported with these techniques, which also suffer from the potentially deleterious presence of repeats in the plasmids. Moreover, these vectors are limited for the size of the DNA sequences that can be engineered into them.

Therefore, numbers of methods have emerged to improve and develop new ways to increase the transgenesis efficiency. Nevertheless, a very limited amount of methods allows better control and numbers of species remain resistant or very inefficient for this technology. Main problems encountered are:

Transgenesis control and efficiency

Early integration events (germ line transmission)

The control of integrated copy number.

SUMMARY

The present invention exactly aims at offering a method allowing to improve the efficiency of DNA's random integration during the transgenesis and to allow a better control of the integrity of the integrated DNA, as well as to reduce the number of copies of integrated DNA.

The method for random integrating an exogenous DNA into the genomic DNA according to the invention consists in linearization of the DNA polynucleotide to be integrated having no 5' and 3' free ends from a vector into the host cell.

The method according to the invention consists in a method for randomly integrating a polynucleotide into a host cell genome by (in vivo or in ovo) preparation into the host cell of said linear polynucleotide having free 5' and 3' ends, said method comprising:

a) Introducing into said host cell a vector having no free 5' and 3' ends and comprising the polynucleotide sequence to be linearized, said vector comprising at least one cleavage site and said cleavage site being found in the host cell genome at less than 5 copies, preferably 2 copies, and more preferably said cleavage site is not found in the host cell genome; and, b) causing cleavage of said site(s) in said host cell, thereby creating or releasing said polynucleotide in a linear form having free 5' and 3' ends from said vector into said host cell; and, c) maintaining the host cell under conditions and for a period of time sufficient to cause the random integration of said linearized polynucleotide into said host cell genome.

Optionally, said method further comprises, prior to step (b), an additional step of introducing into said host cell a cleaving agent or a vector comprising a nucleic acid encoding said cleaving agent. Preferably, said method further comprises, prior to step (b), an additional step of introducing into said host cell said cleaving agent. Optionally, said vector comprising a nucleic acid encoding said cleaving agent is an expression vector or a mRNA. Optionally, said host cell is a transgenic cell expressing said cleaving agent. Said polynucleotide sequence to be integrated according to the present invention is unable to undergo homologous recombination with the host cell genome. Optionally, said polynucleotide to be integrated have less than 70% indentity with a host cell genomic sequence, preferably less than 60 or 50%, more preferably less than 40, 30 or 20% identity. Optionally, the 5' and 3' sequences of said polynucleotide to be integrated have no homology with a host cell genomic sequence, preferably less than 90% indentity, more preferably less than 80 or 70%, still more preferably less than 50, 40, 30 or 20% identity, wherein said 5' and 3' sequences are 5 kb long, preferably between 3 kb and 1.5 kb long, more preferably 1 kb, 500 bp or 100 bp long. Preferably, the cleaved sites do not generate cohesive ends. Preferably, said polynucleotide sequence to be excised does not comprise any cleavage site. Preferably, said vector comprising said polynucleotide sequence to be linearized further comprises said nucleic acid encoding said cleaving agent. Preferably, said polynucleotide sequence is flanked by at least one cleavage site. Preferably, said polynucleotide sequence to be linearized is flanked by two cleavage sites. Preferably, said cleavage site is an endonuclease site and said cleaving agent is the corresponding endonuclease. More preferably, said endonuclease has a recognition site of at least 12 nucleotides. Still more preferably, said endonuclease is a meganuclease, notably one meganuclease of FIG. 2. Optionally, said meganuclease is selected from the group consisting of I-Ceu I, I-Cre I, I-Chu I, I-Csm I, I-Dmo I, I-Pan I, I-Sce I, I-Sce II, I-Sce III, I-Sce IV, F-Sce I, F-Sce II, PI-Aae I, PI-Ape I, PI-Ceu I, PI-Cir I, PI-Ctr I, PI-Dra I, PI-Mav I, PI-Mfl I, PI-Mgo I, PI-Mja I, PI-Mka I, PI-Mle I, PI-Mtu I, PI-MtuH I, PI-Pab III, PI-Pfu I, PI-Pho I, PI-Pko I, PI-Psp I, PI-Rma I, PI-Sce I, PI-Ssp I, PI-Tfu I, PI-Tfu II, PI-Tli I, PI-Tli II, PI-Tsp I, PI-Tsp II, PI-Bsp I, PI-Mch I, PI-Mfa I, PI-Mga I, PI-Mga II, PI-Min I, PI-Mma I, PI-Msh I, PI-Msm II, PI-Mth I, PI-Tag I, PI-Thy II, I-Ncr I, I-Ncr II, I-Pan II, I-Tev I, I-Ppo I, I-Dir I, I-Hmu I, I-Hmu II, I-Tev II, I-Tev II, F-Sce I, F-Sce II (HO), F-Suv I, F-Tev I, and F-Tev II. Preferably, said meganuclease is selected from the group consisting of I-Ceu I, I-Cre I, and I-Sce I. Optionally, said endonuclease is synthetic. Preferably, said vector is a double-stranded DNA vector. Optionally, said vector is a plasmid or a viral vector. Preferably, said vector is a plasmid. Preferably, said polynucleotide sequence is a sequence encoding a polypeptide or an antisense, a regulatory sequence, or a recognition sequence for a molecule. Preferably, said host cell is selected from the group consisting of a stem cell, a somatic cell, a gamete, a blastomer and an egg. More preferably, said host cell is selected from the group consisting of a stem cell, a blastomer and an egg. Optionally, said method for randomly integrating a polynucleotide into a host cell genome is used for stable transfection or transgenesis.

In one embodiment of the present invention, the method consists in a method for randomly integrating a polynucleotide into the host cell genome by (in vivo or in ovo) preparation into the host cell of said linear polynucleotide having free 5' and 3' ends from a vector, said method comprising the following steps:

a) Introducing in said host cell a vector having no free 5' and 3' ends and comprising said polynucleotide sequence to be linearized or excised, said vector comprising at least one endonuclease site and said endonuclease site being found in the host cell genome at less than 5 copies, preferably 2 copies, and more preferably said endonuclease site is not found in the host cell genome;

b) Optionally, introducing in said host cell either the endonuclease which cleaves said endonuclease site present in said vector or an expression vector comprising a nucleic acid encoding said endonuclease; and, c) causing cleavage of said site in said host cell, thereby creating or releasing said polynucleotide in a linear form having free 5' and 3' ends from said vector into said host cell; and, d) maintaining the host cell under conditions and for a period of time sufficient to cause the random integration of said linearized or excised polynucleotide into said host cell genome.

Preferably, step b) consists in introducing in said host cell the endonuclease which cleaves said endonuclease site. Preferably, steps a) and b) are simultaneous. Optionally, said vector comprising a nucleic acid encoding said endonuclease is an expression vector or a mRNA. Optionally, said host cell is a transgenic cell expressing said endonuclease. Said polynucleotide sequence to be integrated according to the present invention is unable to make significantly an homologous recombination with the host cell genome. Optionally, said polynucleotide to be integrated have less than 70% indentity with a host cell genomic sequence, preferably less than 60 or 50%, more preferably less than 40, 30 or 20% identity. Optionally, the 5' and 3' sequences of said polynucleotide to be integrated have no homology with a host cell genomic sequence, preferably less than 90% indentity, more preferably less than 80 or 70%, still more preferably less than 50, 40, 30 or 20% identity, wherein said 5' and 3' sequences are 5 kb long, preferably between 3 kb and 1.5 kb long, more preferably 1 kb, 500 bp or 100 bp long. Preferably, the cleaved sites do not generate cohesive ends. Optionally said vector further comprises a nucleic acid sequence encoding the endonuclease. Optionally, said polynucleotide to be linearized or excised and said nucleic acid encoding said endonuclease are each comprised by a distinct vector. Preferably, said polynucleotide to be linearized or excised does not comprise any endonuclease site. Preferably, said polynucleotide sequence is flanked by at least one endonuclease site. Preferably, said polynucleotide sequence to be linearized is flanked by two endonuclease sites. Preferably, said endonuclease has a recognition site of at least 12 nucleotides. Still more preferably, said endonuclease is a meganuclease, notably one meganuclease of FIG. 2. Optionally, said meganuclease is selected from the group consisting of I-Ceu I, I-Cre I, I-Chu I, I-Csm I, I-Dmo I, I-Pan I, I-Sce I, I-Sce II, I-Sce II, I-Sce IV, F-Sce I, F-Sce II, PI-Aae I, PI-Ape I, PI-Ceu I, PI-Cir I, PI-Ctr I, PI-Dra I, PI-Mav I, PI-Mfl I, PI-Mgo I, PI-Mja I, PI-Mka I, PI-Mle I, PI-Mtu I, PI-MtuH I, PI-Pab III, PI-Pfu I, PI-Pho I, PI-Pko I, PI-Psp I, PI-Rma I, PI-Sce I, PI-Ssp I, PI-Tfu I, PI-Tfu II, PI-Tli I, PI-Tli II, PI-Tsp I, PI-Tsp II, PI-Bsp I, PI-Mch I, PI-Mfa I, PI-Mga I, PI-Mga II, PI-Min I, PI-Mma I, PI-Msh I, PI-Msm II, PI-Mth I, PI-Tag I, PI-Thy II, I-Ncr I, I-Ncr II, I-Pan II, I-Tev I, I-Ppo I, I-Dir I, I-Hmu I, I-Hmu II, I-Tev II, I-Tev III, F-Sce I, F-Sce II (HO), F-Suv I, F-Tev I, and F-Tev II. Preferably, said meganuclease is selected from the group consisting of I-Ceu I, I-Cre I, and I-Sce I. Optionally, said endonuclease is synthetic. Preferably, said vector is double-stranded. Optionally, said polynucleotide can comprise a sequence encoding a polypeptide or an antisense, a regulatory sequence such as promoter and enhancer, and/or a recognition sequence for a molecule. Preferably, said host cell is selected from the group consisting of a stem cell, a somatic cell, a gamete, a blastomer and an egg. More preferably, said host cell is selected from the group consisting of a stem cell, a blastomer and an egg. Optionally, said method for randomly integrating a polynucleotide into a host cell genome is used for stable transfection or transgenesis.

The present invention relates to a composition for transgenesis or for stable transfection comprising:

1) a vector having no 5' and 3' free ends and comprising a transgene to be randomly integrated, said vector comprising at least one cleavage site which is found in the host cell genome at less than 5 copies, preferably 2 copies, and more preferably said cleavage site is not found in the host cell genome; and, 2) a cleaving agent or a vector comprising a nucleic acid encoding said cleaving agent.

Preferably, said composition is used for transgenesis. Preferably, said composition comprises the cleavage agent. Optionally, said vector comprising a nucleic acid encoding said cleaving agent is an expression vector or a mRNA. Said transgene to be integrated according to the present invention is unable to make significantly an homologous recombination with the host cell genome. Optionally, said transgene to be integrated have less than 70% indentity with a host cell genomic sequence, preferably less than 60 or 50%, more preferably less than 40, 30 or 20% identity. Optionally, the 5' and 3' sequences of said transgene to be integrated have no homology with a host cell genomic sequence, preferably less than 90% indentity, more preferably less than 80 or 70%, still more preferably less than 50, 40, 30 or 20% identity, wherein said 5' and 3' sequences are 5 kb long, preferably between 3 kb and 1.5 kb long, more preferably 1 kb, 500 bp or 100 bp long. Preferably, the cleaved sites do not generate cohesive ends. Preferably, said transgene does not comprise any cleavage site. Optionally said vector comprising said transgene further comprises a nucleic acid sequence encoding the cleaving agent. Optionally, said transgene and said nucleic acid encoding said cleaving agent are each comprised by a distinct vector. Preferably, said transgene is flanked by at least one cleavage site. Preferably, said transgene is flanked by two cleavage sites. Preferably, said cleavage site is an endonuclease site and said cleaving agent is the corresponding endonuclease. Preferably, said endonuclease has a recognition site of at least 12 nucleotides. Still more preferably, said endonuclease is a meganuclease, notably one meganuclease of FIG. 2. Optionally, said meganuclease is selected from the group consisting of I-Ceu I, I-Cre I, I-Chu I, I-Csm I, I-Dmo I, I-Pan I, I-Sce I, I-Sce II, I-Sce III, I-Sce IV, F-Sce I, F-Sce II, PI-Aae I, PI-Ape I, PI-Ceu I, PI-Cir I, PI-Ctr I, PI-Dra I, PI-Mav I, PI-Mfl I, PI-Mgo I, PI-Mja I, PI-Mka I, PI-Mle I, PI-Mtu I, PI-MtuH I, PI-Pab III, PI-Pfu I, PI-Pho I, PI-Pko I, PI-Psp I, PI-Rma I, PI-Sce I, PI-Ssp I, PI-Tfu I, PI-Tfu II, PI-Tli I, PI-Tli II, PI-Tsp I, PI-Tsp II, PI-Bsp I, PI-Mch I, PI-Mfa I, PI-Mga I, PI-Mga II, PI-Min I, PI-Mma I, PI-Msh I, PI-Msm II, PI-Mth I, PI-Tag I, PI-Thy II, I-Ncr I, I-Ncr II, I-Pan II, I-Tev I, I-Ppo I, I-Dir I, I-Hmu I, I-Hmu II, I-Tev II, I-Tev III, F-Sce I, F-Sce II (HO), F-Suv I, F-Tev I, and F-Tev II. Preferably, said meganuclease is selected from the group consisting of I-Ceu I, I-Cre I, and I-Sce I. Optionally, said endonuclease is synthetic. Preferably, said vector is double-stranded. Preferably, said vector is a plasmid. Optionally, said transgene can comprise a sequence encoding a polypeptide or an antisense, a regulatory sequence such as promoter and enhancer, and/or a recognition sequence for a molecule.

The invention relates to the use of the composition according to the present invention for producing transgenic cells, non-human animals or plants. Preferably, said non-human animals are selected from non human mammals, birds, reptiles, amphibians and fishes. For example, the invention contemplates cattle (cows), goats, rabbit, rodents, marmots, monkeys, insects (spider, butterflies, fly), fishes, calmar, amphoxius, xenopes, birds, chickens, ascidies and ovine races (sheeps). More particularly, the invention contemplates fishes such as sticklebass, astyanax, medaka and zebrafish, birds like chickens and rodents such as mice.

The present invention also relates to the resulting cells from any method of in vivo or in ovo linearization of a polynucleotide and of random polynucleotide integration according to the present invention and, their uses, for example for production of proteins or other genes, biomolecules, biomaterials, transgenic plants, vaccines, transgenic plants and animals or for treatment or prophylaxis of a condition or disorder in an individual. More particularly, the invention concerns any non-human transgenic animal and any transgenic plant comprising a cell resulting from any method of in vivo linearization of a polynucleotide and of random polynucleotide integration according to the present invention. The invention also relates to any use of a cell, of a non-human transgenic animal or of a transgenic plant according to the present invention for production of protein, antisense, biomolecule, biomaterial, or vaccine. The invention further relates to the use of any resulting cell for treatment or prophylaxis of a condition or disorder in an individual.

Moreover, the invention concerns a method of treating or prophylaxis of a genetic disease in an individual in need thereof by random integration of a polynucleotide comprising the steps of:

a) Introducing in said individual cell a vector having no free 5' and 3' ends and comprising said polynucleotide, said vector comprising at least one cleavage site which is found in the individual cell genome at less than 5 copies, preferably 2 copies, and more preferably said cleavage site is not found in the host cell genome;

b) causing cleavage of said site(s) in said individual cell, thereby creating or releasing said polynucleotide in a linear form having free 5' and 3' ends from said vector into said individual cell; and, c) maintaining the host cell under conditions and for a period of time sufficient to cause the random integration of said linearized or excised polynucleotide into said individual cell genome; said random integration of said polynucleotide compensates the genetic defect causing said genetic disease.

Optionally, said method further comprises, prior to step (b), an additional step of introducing into said individual cell a cleaving agent or a vector comprising a nucleic acid encoding said cleaving agent. Said polynucleotide sequence to be integrated according to the present invention is unable to make significantly an homologous recombination with the host cell genome. Optionally, said polynucleotide to be integrated have less than 70% indentity with a host cell genomic sequence, preferably less than 60 or 50%, more preferably less than 40, 30 or 20% identity. Optionally, the 5' and 3' sequences of said polynucleotide to be integrated have no homology with a host cell genomic sequence, preferably less than 90% indentity, more preferably less than 80 or 70%, still more preferably less than 50, 40, 30 or 20% identity, wherein said 5' and 3' sequences are 5 kb long, preferably between 3 kb and 1.5 kb long, more preferably 1 kb, 500 bp or 100 bp long. Preferably, the cleaved sites do not generate cohesive ends. Preferably, said polynucleotide sequence to be excised does not comprise any cleavage site. Preferably, said vector comprising said polynucleotide sequence to be linearized or excised further comprises said nucleic acid encoding said cleaving agent. Preferably, said polynucleotide sequence to be linearized or excised is flanked by at least one cleavage site. Preferably, said polynucleotide sequence to be linearized or excised is flanked by two cleavage sites. Preferably, said cleavage site is an endonuclease site and said cleaving agent is the corresponding endonuclease. More preferably, said endonuclease has a recognition site of at least 12 nucleotides. Still more preferably, said endonuclease is a meganuclease, notably one meganuclease of FIG. 2. Optionally, said meganuclease is selected from the group consisting of I-Ceu I, I-Cre I, I-Chu I, I-Csm I, I-Dmo I, I-Pan I, I-Sce I, I-Sce II, I-Sce III, I-Sce IV, F-Sce I, F-Sce II, PI-Aae I, PI-Ape I, PI-Ceu I, PI-Cir I, PI-Ctr I, PI-Dra I, PI-Mav I, PI-Mfl I, PI-Mgo I, PI-Mja I, PI-Mka I, PI-Mle I, PI-Mtu I, PI-MtuH I, PI-Pab III, PI-Pfu I, PI-Pho I, PI-Pko I, PI-Psp I, PI-Rma I, PI-Sce I, PI-Ssp I, PI-Tfu I, PI-Tfu II, PI-Tli I, PI-Tli II, PI-Tsp I, PI-Tsp II, PI-Bsp I, PI-Mch I, PI-Mfa I, PI-Mga I, PI-Mga II, PI-Min I, PI-Mma I, PI-Msh I, PI-Msm II, PI-Mth I, PI-Tag I, PI-Thy II, I-Ncr I, I-Ncr II, I-Pan II, I-Tev I, I-Ppo I, I-Dir I, I-Hmu I, I-Hmu II, I-Tev II, I-Tev II, F-Sce I, F-Sce II (HO), F-Suv I, F-Tev I, and F-Tev II. Preferably, said meganuclease is selected from the group consisting of I-Ceu I, I-Cre I, and I-Sce I. Optionally, said endonuclease is synthetic. Preferably, said vector is a double-stranded DNA vector. Optionally, said vector is a plasmid or a viral vector. Preferably, said vector is a plasmid. Preferably, said polynucleotide sequence is a sequence encoding a polypeptide or an antisense, a regulatory sequence, or a recognition sequence for a molecule. Preferably, said individual cell is a stem cell or a somatic cell.

The invention relates to a method for producing a transgenic animal. More particularly, the invention concerns a method for producing a non-human transgenic animal, wherein embryonic stem cells are tranfected by the method according to the present invention and screened for random integration event, the cells are injected into embryos at a stage at which they are capable of integrating the transfected cells, for example at the blastocyst stage, the embryos are then reimplanted in a surrogate mother, and the chimeric individuals obtained at the end of gestation, and in which colonization by embryonic stem cells of the germline is observed are mated to obtain transgenic animals. Otherwise, the invention concerns a method for producing a non-human transgenic animal, wherein fertilized egg are tranfected by the method according to the present invention, and either the eggs are reimplanted in a surrogate mother and the transgenic individuals obtained at the end of gestation or the eggs are incubated in condition appropriate for the developing of the transgenic animal.

BRIEF DESCRIPTION OF THE DRAWINGS

FIG. 2 is a table disclosing the known meganuclease. Th means theorical, Exp experimental demonstration, and Pot potential.

FIG. 4 is a schematic diagram of the DNA constructs described in the Example 1. "I-Sce I" refers to I-Sce I endonuclease recognition and cleavage site. "IR" refers to invert repeat. "pA$_{SV40}$" refers to the polyadenylation signal of SV40.

FIG. 6 is a half-tome reproduction of an electrophoresis gel from the southern analysis after a EcoR V digestion of the transfected cell genome with both pVirtkU3Rβgeo and pCMV-I SceI and a diagram describing the obtained restriction fragment. +IN means that the cells were also transfected with a plasmid encoding an integrase. If one copy of the fragment ΔU$_3$RβgeopA$_{SV40}$ is integrated in the cell genome, the Southern analysis shows one band at 1.2 kb and another one of at least 2.5 kb. If the fragment ΔU$_3$RβgeopA$_{SV40}$ is integrated in the cell genome with at least two consecutive copies, the Southern analysis shows at least one band at 1.2 kb and one band at 2.5 kb.

Figure 1:
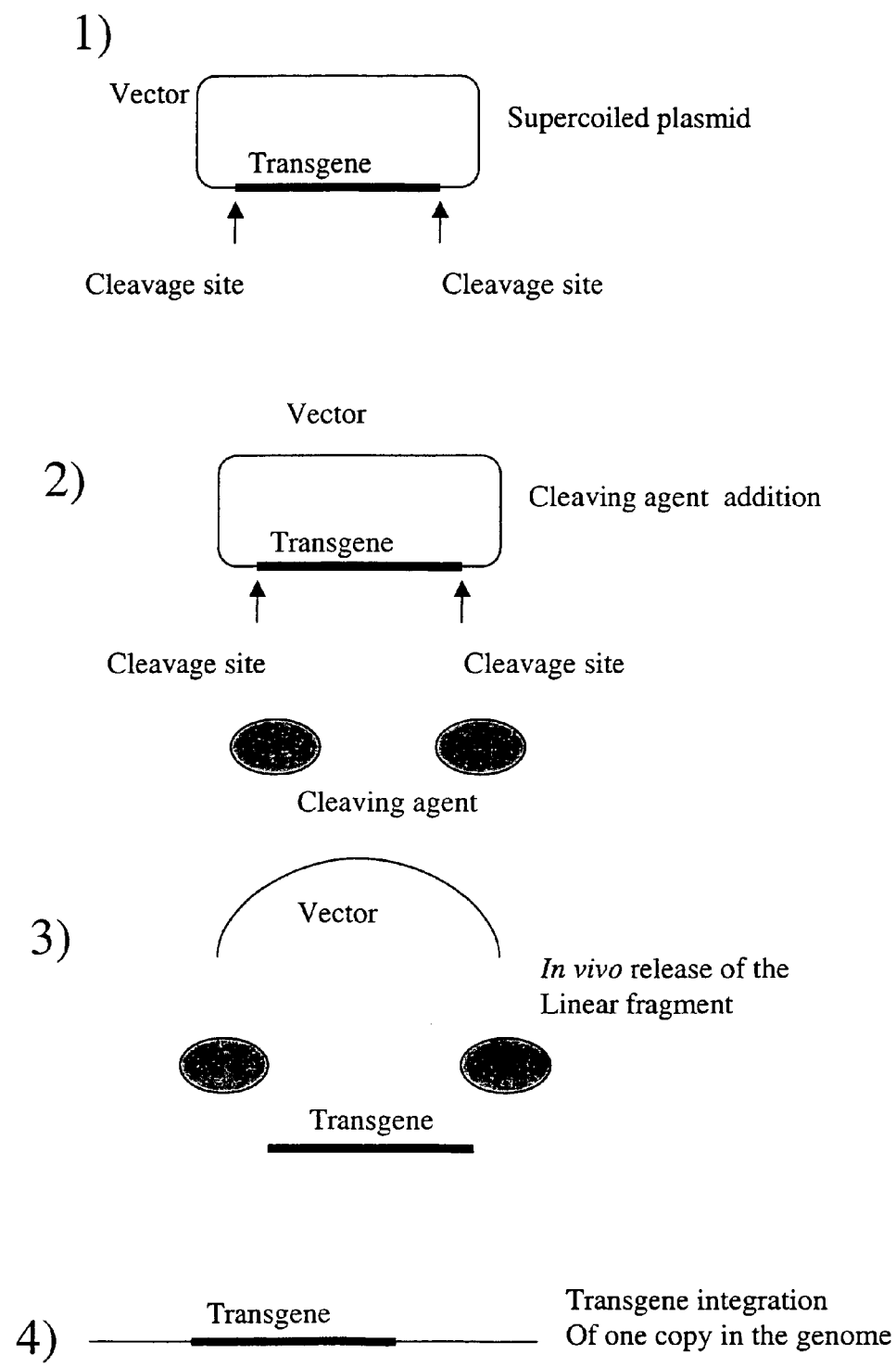
FIG. 1 is a schematic diagram representing one embodiment of the method for integrating a transgene, said transgene being in vivo released from a supercoiled plasmid vector. The transgene is flanked by two cleavage sites. The cleavage agent is added and makes in vivo a double-stranded break at the two cleavage sites. The linear transgene is released and one copy of the transgene is integrated into the genome.

COS cells were stably transfected with the in vivo linearization method.

The structure of the ppSNIE construct included HindIII and I-Sce I cleavage sites (I-SceICS) as well as the NEO probe (Probe).

Southern Blot analysis were performed of a co-transfection with the plasmids ppSNIE and pCMV-I-SceI (−) as well as a co-transfection with the plamsids ppSNIE and pCMV-I-SceI (+).

Transient expression of GFP in α-actin-GFP injected embryos was confirmed.

GFP transient expression was improved when the meganuclease is added to the injection buffer. Dechorionated embryos were shown to express GFP at different levels. For routine observations, chorions are not removed.

The efficiency of transgenesis in medaka following injection of p☐act-GFPM2 was demonstrated. A Southern blot analysis of insert structures in p☐act-GFPM2 lines injected with or without the meganuclease was performed with a probe obtained with Xhol and EcoRV digests and corresponding to the actin promoter and the GFP reporter gene. On Southerns, two fragments of 1 and 2 kb corresponding respectively to the GFP/pA and to the downstream region of the actin promoter (3'☐p) were observed. 5'☐p+pBluSK: 4,8 kb band, diagnostic of the upstream region of the promoter linked with the plasmid sequence.

A strong promoter (promoter of the mouse Gas 5 gene) was used in a Megafluo plasmid construct to direct the transcription of a fluorescent reporter (the DSRed1-E5 from Clontech). Two I-Sce I recognition/cleavage sites in the same orientation flanking the transgene were subcloned in a derivate of pUC vector.

A I-Sce I expressing vector (pI-SceI/EGFP) was produced. The I-Sce I protein coding sequence was subcloned into the MCS of pIRES2-EGFP (Clontech). The CMV promoter was used to drive the transcription from a single RNA of both I-Sce I protein and the EGFP fluorescent reporter as a bicistronic expression.

Meganuclease mediated transgenesis was performed by in ova linearization of the transgene by an I-SceI expressing vector.

An agarose gel was produced showing the genomic DNA extraction of three-weeks old mice and of stillborn mice. About 500 ng of DBA were loaded on a 1% TAE agarose gel. Genomic DNA from stillborn animals were degraded as expected from dead animal but DNA was still available for a PCR analysis.

An agarose gel of the PCR amplification of a mouse β-globin gene fragment and of the reporter sequence of Megafluo (Red5) was produced including all genomic DNA samples wherein the 494 bp PCR product expected for the β-globin gene was detected. Animals 1 and 25 and the stillborn animal A are transgenics as the 484 bp fragment of the Megafluo reporter gene (DSRedE1-5) are detected. Genomic DNA extraction of three-weeks old mice was included as were genomic DNA extraction of stillborn mice. Negative control corresponds to the pI-SceI/EGFP plasmid while the positive control corresponds to megafluo plasmid. Wild type corresponds to genomic DNA extracted from B6SJL uninjected mice and a contamination control performed without DNA was included.

An agarose gel showing the PCR amplification of a sub-fragment of the pI-Sce I/EGFP was produced. Positive control corresponded to pI-SceI/EGFP plasmid. Wild type corresponded to genomic DNA extracted from B6SJL uninjected mice. Control corresponded to PCR contamination control performed without DNA.

Classical transgenesis was demonstrated with an agarose gel showing the PCR amplification of the reporter sequence of Megaflu (Red5) which included samples from the 8 newborn.

The plasmid constructs used for the meganuclease mediated transgenesis by in ovo linearization of the transgene by an PI-SceI expressing vector included the Gas5 promoter to drive the expression of the reporter gene LagoZ (a nearly CPG-free LacZ sequence). These two sequences were flanked by two PI-SceI recognition/cleaving sites on the same orientation separating the backbone sequences of the vector. A single recognition/cleaving I-SceI site was present in between the promoter and the reporter gene.

The results of the meganuclease mediated transgenesis by in ovo linearization of the transgene by I-Sce I or PI-Sce I protein with the PIFF-Lago construct were demonstrated with an agarose gel showing the PCR results of a fragment of the reporter gene (LagoZ). Positive control corresponds to PIFFLago plasmid. Wild type coresponds to genomic DNA from B6SJL uninjected mouse. Control corresponds to PCR contamination control performed without DNA.

PCR genotyping on the genomic DNAs of the nine 12 dpi-embryos injected with PIFFLago plasmid plus I-SceI protein was performed. The 370 bp PCR product of the Lago reporter was detected in four out of nine embryos (number 101, 102, 103, 105).

PCR genotyping on the genomic DNAs of the nine 14 dpi-embryos injected with PIFFLago plasmid plus PI-SceI protein was performed. The 370 bp PCR product of the Lago reporter was detected in three out ten embryos (number 111, 112, 114).

The results of the meganuclease mediated transgenesis by in ovo linearization of the transgene by I-Sce I protein with the PIFF-Lago construct were demonstrated with Southern blot analysis.

Genotyping of the nine 12 dpi-embryos injected with PIFFLago plasmid plus I-SceI protein is performed by Southern Blot experiments. Genomic DNAs were digested with EcoRI restriction enzyme. Two different digoxigenine-labelled probes were used; one hybridizing to the Gas5 sequences and the second to the Lago reporter gene. Detection is performed with the chemioluminescent CDP-Star (Roche) substrate on hyperfilm ECL films (Amersham). A 3.1 kbp fragment is detected with the Gas5 probe and corresponds to the endogenous mouse Gas5 gene. Animals 105, 103 and 101 are transgenics as an additional band is detected. This fragment is as well detected when the blot is deshybridized and reprobed with the Lago probe.

DETAILED DESCRIPTION

Definitions

By <<transgenesis>> is intended the introduction of new DNA sequences into the genome, preferably resulting in the production of transgenic animals or plants.

As used interchangeably herein, the terms "nucleic acid" "oligonucleotide", and "polynucleotide" include RNA, DNA, or RNA/DNA hybrid sequences of more than one nucleotide in either single chain or duplex form. The term "polynucleotide" refers to a polymer of units comprising a purine or pyrimidine, a ribose or deoxyribose sugar moiety, and a phosphate group, or phosphodiester linkage. "polynucleotides" also refers to polynucleotide comprising "modified nucleotides" which comprise at least one of the following modifications (a) an alternative linking group, (b) an analogous form of purine, (c) an analogous form of pyrimidine, or (d) an analogous sugar.

By <<in vivo>> is intended in a cell, said cell being isolated or comprised in an organism. The term <<in vivo>> encompasses <<in ovo>>. By <<in ovo>> is intended in an egg.

Flanked: A polynucleotide to be linearized or excised is flanked by a cleavage site if such a site is present at or near either or both ends of the polynucleotide. There can be one cleavage site present or near one end of the polynucleotide to be linearized or excised or there can be two cleavage sites, one at or near each end of the polynucleotide to be linearized or excised. By "near" is preferably intended in the present invention that the cleavage site is located at less than 1 kb, preferably less than 500 bp, more preferably less than 200, or 100 bp, of the end of the polynucleotide to be integrated.

By cleavage, cleaving is intended in the present invention the formation of a DNA double-stranded break. By "cleaving agent" is intended the agent able to cleave the "cleavage site".

By "endonuclease" is intended an enzyme which makes a double-stranded break in the DNA molecule at highly specific locations. This endonuclease can be natural. Preferably the enzyme is a homing endonuclease or a meganuclease. This endonuclease can also be synthetic.

By "biomolecule" is intended in the present invention any organic molecule that is an essential part of a living organism such as polypeptide, protein, DNA or RNA polynucleotide.

By "free ends" is intended blunt ends and 5' or 3' overhangs available for exonuclease degradation. Therefore, in the case of a linear molecule, any modification of the 5' and 3' abolishing or significatively decreasing the exonuclease degradation will not be considered as free ends. For example, a linear polynucleotide comprising secondary structures or modified nucleotides at its extremities conferring a exonuclease resistance is not considered as having free ends.

"Cells," or "host cells", are terms used interchangeably herein. It is understood that such terms refer not only to the particular subject cell but to the progeny or potential progeny of such a cell. Because certain modifications may occur in succeeding generations due to either mutation or environmental influences, such progeny may not be identical to the parent cell, but are still included within the scope of the term as used herein. The cell can be a stem cell (preferably an embryonic stem cell), a somatic cell, a gamete, a blastomer and an egg (preferably a fertilized egg).

By <<exogenous polynucleotide>> is intended a polynucleotide without any similarity with the host cell chromosome. By <<no similarity>> is intended less than 50% identity, preferably 40 or 30% identity, more preferably less than 20% identity with one sequence of the host cell chromosome. The polynucleotide similarity is so low that the polynucleotide is unable to make homologous recombination with the host cell chromosome.

"Identity" refers to sequence identity between two nucleic acid molecules. Identity can be determined by comparing a position in each sequence which may be aligned for purposes of comparison. When a position in the compared sequence is occupied by the same base, then the molecules are identical at that position. A degree of similarity or identity between nucleic acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default settings.

As used herein, the term "transgene" means a nucleic acid sequence (or an antisense transcript thereto) which has been introduced into a cell genome. A transgene could be partly or entirely heterologous, i.e., foreign, to the transgenic animal/plant or cell into which it is introduced; or, is homologous to an endogenous gene of the transgenic animal or cell into which it is introduced, but it is inserted into the animal's genome at a location which differs from that of the natural gene. A transgene can include one or more transcriptional regulatory sequences and any other nucleic acid, such as introns, that may be necessary for optimal expression of a selected nucleic acid. Throughout the present invention, the polynucleotide to be linearized or excised and integrated is a transgene.

The "non-human animals" or "transgenic animals" of the invention include in, but not restrictive to, mammalians such as rodents, non-human primates, sheep, dog, cow, chickens, amphibians, reptiles, fishes, ascidies. Preferred non-human animals are selected from the rodent family including rat and mouse, most preferably mouse, though transgenic amphibians, such as members of the Xenopus genus, and transgenic chickens, cow, sheep, and fishes can also provide important tools.

A "transgenic animal" or "transgenic plant" refers to any animal or plant, in which one or more of the cells of the animal or plant contain a transgene introduced by way of human intervention, such as by transgenic techniques well known in the art. The transgene is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule is integrated within a chromosome. Moreover, "transgenic animal" or "transgenic plant" also includes those recombinant animals or plants in which gene disruption of one or more genes is caused by human intervention, including antisense technique. By transgenic animal is also intended transgenic embryo.

The term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". A vector according to the present invention comprises, but is not limited to, a YAC (yeast artificial chromosome), a BAC (bacterial artificial), a baculovirus vector, a phage, a phagemid, a cosmid, a viral vector, a plasmid, a RNA vector or a linear or circular DNA or RNA molecule which may consist of a chromosomal, non chromosomal, semi-synthetic or synthetic DNA. In general, expression vectors of utility in recombinant DNA techniques are often in the form of "plasmids" which refer generally to circular double stranded DNA loops which, in their vector form are not bound to the chromosome. Large numbers of suitable vectors are known to those of skill in the art and commercially available, such as the following bacterial vectors: pQE70, pQE60. pQE-9 (Qiagen), pbs, pDIO, phagescript, psiXI74. pbluescript SK. pbsks. pNH8A. pNH16A, pNH18A, pNH46A (Stratagene); ptrc99a, pKK223-3, pKK233-3, pDR540, pRIT5 (Pharmacia); pWLNEO. pSV2CAT, pOG44, pXT1, pSG (Stratagene); pSVK3, pBPV, pMSG, pSVL (Pharmacia); pQE-30 (QIAexpress).

Viral vectors include retrovirus, adenovirus, parvovirus (e.g., adenoassociated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, Dtype viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in McVey et al., U.S. Pat. No. 5,801,030, the teachings of which are incorporated herein by reference.

Vectors according the present invention can comprise transposon (Ivicz et al. 1997, *Cell*, 91, 501–510; Raz et al, 1998, *Current Biology*, 8, 82–88; the disclosure of which is incorporated herein by reference).

Vectors can comprise selectable markers (for example, neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine-guanine phosphoribosyl transferase for eukaryotic cell culture; TRP1 for *S. cerevisiae;* tetracycline, rifampicin or ampicillin resistance in *E. coli*; etc . . . ). However, the invention is intended to include such other forms of expression vectors which serve equivalent functions and which become known in the art subsequently hereto.

General Overview of the Invention

The present invention exactly aims at offering a method allowing to improve the efficiency of DNA's random integration during the transgenesis or the stable transfection and to allow a better control of the integrity of the integrated DNA, as well as to reduce the number of copies of integrated DNA. The more interesting application of the present invention is the transgenesis, more particularly in species in which the transgenesis process are unefficient.

The method according to the invention consists in (in vivo) linearization or excision into the host cell of the DNA polynucleotide to be integrated in the host cell genome (see FIG. 1). The invention concerns a method for randomly integrating an exogenous DNA into the genomic DNA of the host cell wherein the polynucleotide to be integrated is linearized or excised in vivo from a vector. The in vivo linearization or excision of the polynucleotide to be integrated allows to generate a linear fragment with free ends available for recombining with the genomic DNA of the host cell. According to this method, said vector has no free ends allowing the protection of the transgene against the degradation. The method according to the present invention does not use the homologous recombination. The polynucleotide integration is random and not targeted.

Therefore, the invention concerns a method for in vivo generation of a linear polynucleotide with 5' and 3' free ends, corresponding essentially to the transgene, from polynucleotide having no free end, said linear polynucleotide being randomly integrated into the host cell genome. In a particular embodiment of this method, said polynucleotide is comprised by the vector having a cleavage site, wherein said cleavage site is found in the host cell genome at less than 5 copies, preferably 2 copies, and more preferably said cleavage site is not found in the host cell genome. In a preferred embodiment of this method, said polynucleotide is comprised by the vector and is flanked by a cleavage site, wherein said cleavage site is found in the host cell genome at less than 5 copies, preferably 2 copies, and more preferably said cleavage site is not found in the host cell genome. Preferably, the cleaved site does not generate cohesive ends. Preferably, said polynucleotide to be in vivo linearized or excised does not comprise any cleavage site. Optionally said vector further comprises a nucleic acid sequence encoding the cleaving agent. Preferably, said cleavage site is a endonuclease site and said cleaving agent is the corresponding endonuclease. Optionally, the nucleic acid encoding the cleaving agent is comprised by an expression vector. Optionally, the nucleic acid encoding the cleaving agent is a mRNA. Optionally, said polynucleotide can comprise a sequence encoding a polypeptide or an antisense, a regulatory sequence such as promoter and enhancer, and/or a recognition sequence for a molecule.

The method according to the invention consists in a method for randomly integrating a polynucleotide into the host cell genome by in vivo preparation said linear polynucleotide having free 5' and 3' ends from a vector, said method comprising the following steps:

a) Introducing in said host cell a vector having no free 5' and 3' ends and comprising said polynucleotide, said vector comprising at least one cleavage site which is found in the host cell genome at less than 5 copies, preferably 2 copies, and more preferably said cleavage site is not found in the host cell genome;

b) causing cleavage of said site(s) in said host cell, thereby creating or releasing said polynucleotide in a linear form from said vector having free 5' and 3' ends into said host cell; and, c) maintaining the host cell under conditions and for a period of time sufficient to cause the random integration of said linearized or excised polynucleotide into said host cell genome.

Preferably, the method according to the invention consists in a method for randomly integrating a polynucleotide into the host cell genome by in vivo preparation said linear polynucleotide having free 5' and 3' ends from a vector, said method comprising the following steps:

a) Introducing in said host cell a vector having no free 5' and 3' ends and comprising said polynucleotide, said polynucleotide being flanked at least one cleavage site which is found in the host cell genome at less than 5 copies, preferably 2 copies, and more preferably said cleavage site is not found in the host cell genome;

b) causing cleavage of said site(s) in said host cell, thereby creating or releasing said polynucleotide in a linear form from said vector having free 5' and 3' ends into said host cell; and, c) maintaining the host cell under conditions and for a period of time sufficient to cause the random integration of said linearized or excised polynucleotide into said host cell genome.

In one embodiment of the present invention, the method for randomly integrating a polynucleotide into the host cell genome by in vivo preparation of said linear polynucleotide having free 5' and 3' ends from a vector comprises the following steps:

a) Introducing in said host cell a vector having no free 5' and 3' ends and comprising said polynucleotide, said polynucleotide being flanked by at least one cleavage site which is found in the host cell genome at less than 5 copies;

b) Introducing the cleaving agent or a vector encoding said cleaving agent; and, c) causing cleavage of said site(s) in said host cell, thereby creating or releasing said polynucleotide in a linear form from said vector having free 5' and 3' ends into said host cell; and, d) maintaining the host cell under conditions and for a period of time sufficient to cause the random integration of said linearzed or excised polynucleotide into said host cell genome.

In a further embodiment of the present invention, the method for randomly integrating a polynucleotide into the host cell genome by in vivo preparation of said linear polynucleotide having free 5' and 3' ends from a vector comprises the following steps:

a) Introducing in said host cell:
a vector having no free 5' and 3' ends and comprising said polynucleotide, said polynucleotide being flanked by at least one cleavage site which is found in the host cell genome at less than 5 copies; and,
the cleaving agent;

b) causing cleavage of said site(s) in said host cell, thereby creating or releasing said polynucleotide in a linear form from said vector having free 5' and 3' ends into said host cell; and, c) maintaining the host cell under conditions and for a period of time sufficient to cause the random integration of said linearzed or excised polynucleotide into said host cell genome.

The process of the invention is remarkable because the release of the polynucleotide to be integrated can only be done in vivo after the crossing of the plasmidic membrane of the host cell, presumably within the nucleus. After the crossing of the plasmidic membrane, the release of the ends of the polynucleotide, preferably by the endonuclease, can be achieved at any moment or in any compartment of the host cell.

Surprisingly, the integrity of the polynucleotide to be integrated is maintained, the efficiency of the transgenesis is significantly increased compared to either circular DNA or in vitro linearized DNA and the polynucleotide is integrated at a very low copy number. For mice, the rate of transgenesis is increased by 3 to 5 times with the method according to the present invention. Moreover, the integrity of the transgene is excellent and the transgene is often integrated in the cell genome at less than three copies, more frequently only one copy. By conventional methods, at least 10 to 20 copies are integrated as a concantemer and, if only one copy is integrated, which is very rare event, the integrity of the transgene is not maintained.

More particularly, the present disclosure shows that meganuclease-mediated transgenesis is indeed a very simple technique that is spectacularly more efficient than the other methods currently reported in fish. The method according to the present invention allows to efficiently integrate DNA in the fish genome, more particularly the medakafish (Oryzias latipes) or zebrafish (Danio rerio) genome (see Example 2). The expression of the transgene is spectacularly improved. Even more striking is the dramatic increase in germline transmission. Whereas in classical egg injection experiments, it does not, in most cases, exceed a few percents, due to late chimeric integrations, the frequency of germline transmission in fish co-injected with the meganuclease was boosted to 50%, suggesting that a single insertion occurred at one-cell stage of the founder fish. Moreover, single low copy integrations occur in most cases. Therefore, meganuclease-induced in ovo linearisation, by limiting degradation of preintegrative DNA free ends, is a simple and efficient process to improve transgenesis by egg injection. Moreover, the generation of polynucleotide free-ends in cell may created recombination foci which could improve the transgene integration.

Therefore, the method according to the present invention presents several advantages among which the increase of the efficiency of the transgenesis or of the stable transfection and the decrease of the copy number of the integrated polynucleotide.

The method according to the present invention concerns the random integration of the transgene. Therefore, the transgene is not designed to undergo homologous recombination with the host cell genome. The 5' and 3' sequence of the polynucleotide to be integrated into the genome do not have significant homologies with one locus of the host genome. Optionally, said polynucleotide to be integrated have less than 70% indentity with a host cell genomic sequence, preferably less than 60 or 50%, more preferably less than 40, 30 or 20% identity. Optionally, the 5' and 3' sequences of said polynucleotide to be integrated have less than 90% indentity with a host cell genomic sequence, preferably less than 80 or 70%, more preferably less than 50, 40, 30 or 20% identity, wherein said 5' and 3' sequences are less than 5 kb long, preferably less than 3 kb or 1.5 kb long, more preferably less than 1 kb, 500 bp or 100 bp long.

For introducing a transgene in a mouse egg by homologous recombination, the man skilled in the art usually flanks the transgene with about 5 kb of homologous sequence, never less than 3 kb. The homologous recombination in egg is a extremely rare event. Indeed, with 5 kb of homologous sequence, the homologous recombination occurs in only 1 clone among 10 millions of fertilized eggs. In embryonic fish cells, homologous recombination never occurs, more particularly in fish fertilized egg.

For transgenesis, the cleaving agent is preferably co-injected with the vector comprising the transgene. Indeed, a co-injection of the cleaving agent avoids the delay due to the expression of the cleaving agent. An early integration of the transgene is important for decreasing the mosaïcism.

In one embodiment of the present invention, the method consists in a method for randomly integrating a polynucleotide into the host cell genome by in vivo preparation said linear polynucleotide having free 5' and 3' ends from a vector, said method comprising the following steps:

a) Introducing in said host cell a vector having no free 5' and 3' ends and comprising said polynucleotide, said polynucleotide being flanked by at least one endonuclease site which is found in the host cell genome at less than 5 copies, preferably less than 2, more preferably never found in the host cell genome;

b) Optionally, introducing in said host cell either the endonuclease which cleaves said endonuclease site present in said vector or a vector comprising a nucleic acid encoding said restriction endonuclease; and, c) causing cleavage of said site(s) in said host cell, thereby creating or releasing said polynucleotide in a linear form having free 5' and 3' ends from said vector into said host cell; and, d) maintaining the host cell under conditions and for a period of time sufficient to cause the random integration of said excised polynucleotide into said host cell genome.

In a particular embodiment of this method, said polynucleotide to be linearized or excised is flanked by two endonuclease sites. Preferably, the step b) consists in introducing in said host cell the endonuclease which cleaves said endonuclease site present in said vector. Preferably, steps a) and b) are simultaneous. Preferably, the cleaved sites do not generate cohesive ends. Optionally said vector further comprises a nucleic acid sequence encoding the endonuclease. Optionally, said polynucleotide to be linearized or excised and said nucleic acid encoding said endonuclease are each comprised by a distinct vector. Preferably, said polynucleotide to be linearized or excised does not comprise any cleavage site. Preferably, said vector is double-stranded. Optionally, said polynucleotide can comprise a sequence encoding a polypeptide or an antisense, a regulatory sequence such as promoter and enhancer, and/or a recognition sequence for a molecule. Preferably, said host cell is selected from the group consisting of a stem cell, a somatic cell, a gamete, a blastomer and an egg.

The present invention relates to a composition for transgenesis comprising:

1) a vector having no 5' and 3' free ends and comprising a transgene to be integrated, said transgene being flanked by at least one cleavage site which is found in the host cell genome at less than 5 copies, preferably 2 copies, and more preferably said cleavage site is not found in the host cell genome; and, 2) a cleaving agent or a vector comprising a nucleic acid encoding said cleaving agent.

Preferably, said composition comprises the cleaving agent. Optionally, said vector comprising a nucleic acid encoding said cleaving agent is an expression vector or a mRNA. Said transgene to be integrated according to the present invention is unable to make significantly an homologous recombination with the host cell genome. Optionally, said transgene to be integrated have less than 70% indentity with a host cell genomic sequence, preferably less than 60 or 50%, more preferably less than 40, 30 or 20% identity. Optionally, the 5' and 3' sequences of said transgene to be integrated have no homology with a host cell genomic sequence, preferably less than 90% indentity, more preferably less than 80 or 70%, still more preferably less than 50, 40, 30 or 20% identity, wherein said 5' and 3' sequences are 5 kb long, preferably between 3 kb and 1.5 kb long, more preferably 1 kb, 500 bp or 100 bp long. Preferably, the cleaved sites do not generate cohesive ends. Preferably, said transgene does not comprise any cleavage site. Optionally said vector comprising said transgene further comprises a nucleic acid sequence encoding the cleavage agent. Optionally, said transgene and said nucleic acid encoding said cleavage agent are each comprised by a distinct vector. Preferably, said transgene is flanked by two cleavage sites. Preferably, said cleavage site is an endonuclease site and said cleaving agent is the corresponding endonuclease. Preferably, said endonuclease has a recognition site of at least 12 nucleotides. Still more preferably, said endonuclease is a meganuclease, notably one meganuclease of FIG. 2. Optionally, said meganuclease is selected from the group consisting of I-Ceu I, I-Cre I, I-Chu I, I-Csm I, I-Dmo I, I-Pan I, I-Sce I, I-Sce II, I-Sce III, I-Sce IV, F-Sce I, F-Sce II, PI-Aae I, PI-Ape I, PI-Ceu I, PI-Cir I, PI-Ctr I, PI-Dra I, PI-Mav I, PI-Mfl I, PI-Mgo I, PI-Mja I, PI-Mka I, PI-Mle I, PI-Mtu I, PI-MtuH I, PI-Pab III, PI-Pfu I, PI-Pho I, PI-Pko I, PI-Psp I, PI-Rma I, PI-Sce I, PI-Ssp I, PI-Tfu I, PI-Tfu II, PI-Tli I, PI-Tli II, PI-Tsp I, PI-Tsp II, PI-Bsp I, PI-Mch I, PI-Mfa I, PI-Mga I, PI-Mga II, PI-Min I, PI-Mma I, PI-Msh I, PI-Msm II, PI-Mth I, PI-Tag I, PI-Thy II, I-Ncr I, I-Ncr II, I-Pan II, I-Tev I, I-Ppo I, I-Dir I, I-Hmu I, I-Hmu II, I-Tev II, I-Tev III, F-Sce I, F-Sce II (HO), F-Suv I, F-Tev I, and F-Tev II. Preferably, said meganuclease is selected from the group consisting of I-Ceu I, I-Cre I, and I-Sce I. Optionally, said endonuclease is synthetic. Preferably, said vector is double-stranded. Preferably, said vector is a plasmid. Optionally, said transgene can comprise a sequence encoding a polypeptide or an antisense, a regulatory sequence such as promoter and enhancer, and/or a recognition sequence for a molecule.

The invention relates to the use of the composition according to the present invention for producing transgenic cells, animals or plants.

Cleavage Site and Cleaving Agent

The cleavage site according to the present invention is preferably not found in the genome of the host cell. If this cleavage site exists in the cell genome, the cell genome presents no more than 5, preferably 2, sites. If some other cleavage sites than the flanking sites exist in the vector, they are preferably located outside of the region comprising the polynucleotide to be linearized or excised.

The cleavage site according to the invention is a sequence or an element which is specific of the cleaving agent. The cleaving agent can be for example a ribozyme, an endonuclease. Preferably, the cleaving agent is an endonuclease. The cleavage site according to the invention could be a modified nucleotide leading under the appropriate conditions to DNA cleavage. Such modified nucleotide could be for example an abasic nucleotide (Lhomme et al, 1999, *Biopolymer*, 52, 65–83; the disclosure of which is incorporated herein by reference). The presence of an abasic nucleoide leads to a cleavage, for example, by the action of AP-endonuclease such as exonuclease III.

In a particular embodiment of the present invention, two or more different endonucleases can be used in the present method. The polynucleotide to be integrated is flanked for example by two different endonuclease sites and the method comprises a step of introducing each endonucleases or one or several vector(s) encoding the used endonucleases.

Preferably, the sites flanking the polynucleotide sequence to be integrated do not generate cohesive ends after the cleavage. Therefore, if the cleavage of the sites could lead to the generation of cohesive ends, the sites have preferably an inverse orientation so as to avoid the multimerization through the cohesive ends.

The endonuclease need to be chosen so as to generate in the genome of the host cell a very low number of cleavages that can be easily repaired by the cell without any damage for this cell. Indeed, the cell without any damage could tolerate a very low number of cleavages in the chromosome, generally less than 5 double-stranded breaks, more preferably less than 2 double-stranded breaks. Preferably, the endonuclease is chosen so as not to generate any double-stranded break in the host cell chromosome.

Commonly used four and six base cutting restriction enzymes are not convenient for the present invention since they would usually lead to cleavage of chromosomal DNA and to cells death due to the existence of many restriction sites within the cellular DNA.

Preferably, the endonuclease sites flanking the polynucleotide sequence to be linearized or excised according to the invention do not naturally occur in the host cell. Preferably, if the vector comprising the polynucleotide sequence to be linearized or excised is a plasmid, the flanking endonuclease sites do not occur in the bacteria used for the plasmid production. Preferably, the flanking endonuclease sites correspond to endonucleases having a recognition site of at least 10, 12, 15, 18, 20, 22 or 25 nucleotides. In a particular embodiment, an endonuclease used in the present invention can tolerate less than 10% of change in its recognition site, preferably 5%, more preferably 2%.

A homing endonuclease or meganuclease which recognizes a large DNA sequence is an example of an endonuclease which can be used in the present invention (Dalgaard et al, 1997, *Nucleic Acids Resarch*, 25, 4626–463; Chevalier et Stoddard, 2001, *Nucleic Acids Resarch*, 29, 3757–3774). An example of a meganuclease enzyme is I-Sce I which recognizes a 18 bp site that does not appear to be represented in murine or human DNA. I-SceI generates a 4 bp staggered cut with 3'OH overhangs. For more information on I-SceI meganuclease, see U.S. Pat. No. 6,238,924, the teaching of which is incorporated herein by reference. In a preferred embodiment, the method according to the present invention uses I-Sce I endonuclease and the corresponding recognition and cleavage site.

Meganucleases constitute a family of very rare-cutting enzymes. See FIG. 2 for a list of meganucleases. Homing endonucleases encoded by introns ORF, independent genes or intervening sequences (inteins) are defined now as "meganucleases". They have recognition sequences that span 12–40 bp of DNA, whereas "classical" restriction enzymes recognise much shorter stretches of DNA, in the 3–8 bp range (up to 12 bp for rare-cutter). Meganucleases are rather well characterised structurally and mechanistically. They fall into 4 separated families on the basis of pretty well conserved amino acids motifs.

1—The Dodecapeptide Family (Dodecamer, DOD, D1-D2, LAGLI-DADG, P1-P2)

This is the largest family of proteins (more than 150 sequences) clustered by their most general conserved sequence motif: one (5 sequences) or two copies (vast majority) of a twelve-residue sequence: the di-dodecapeptide. Meganucleases with one dodecapetide (D) are around 20 kDa in molecular mass and act as homodimer. Those with two copies (DD) range from 25 kDa (230 AA) to 50 kDa (HO, 545 AA) with 70 to 150 residues between each motif and act as monomer.

2—GIG Family

The jointly motif is short but pretty well conserved: KSGIY (10/11 AA) YIGS. For these meganucleases (28 sequences) the cleavage site is different from the recognition sequence.

3—HC Family

Sequences in this group are rich in Histidines and Cysteines residues and the conserved sequence is approximately: "SHLC-G-G-H-C". The most well characterised enzyme: I-Ppo I 4—HNH Family and No Motif The last group of sequences, assembled because they don't have any of previous motifs are not structurally well characterised. The consensus sequence (HH-N-H-H in a window of 35 amino acid residues) is rather complicate. Several properties of these proteins are distinctive from other Meganucleases because they leave a 5' extension of 2 bp after a double-stranded break or have a long size of staggered cut of at least 10 nucleotides. (Most of the Meganucleases cleaves the two strands of a double-stranded DNA and leave a 4 base pair 3' protruding end)

The different classes are summarised:

CLASSE I which are chraracterized by: One Dodecapeptide motif (D1, LAGLI, P1) or two Dodecapeptide motifs (D1-D2, LAGLI-GDAG, P1-P2); and, Cleavage inside the recognition site, leaving 4 nt staggered cut with 3'OH overhangs. There are 8 sub-families including:

One Dodecapeptide motif: Some examples are I-Ceu I, I-Cre I Two Dodecapeptide motif: Some examples are I-Chu I, I-Csm I, I-Dmo I, I-Pan I, I-Sce I, I-Sce II, I-Sce II, I-Sce IV, F-Sce I, F-Sce II, PI-Aae I, PI-Ape I, PI-Ceu I, PI-Cir I, PI-Ctr I, PI-Dra I, PI-Mav I, PI-Mfl I, PI-Mgo I, PI-Mja I, PI-Mka I, PI-Mle I, PI-Mtu I, PI-MtuH I, PI-Pab III, PI-Pfu I, PI-Pho I, PI-Pko I, PI-Psp I, PI-Rma I, PI-Sce I, PI-Ssp I, PI-Tfu I, PI-Tfu II, PI-Tli I, PI-Tli II, PI-Tsp I, PI-Tsp II, PI-Bsp I, PI-Mch I, PI-Mfa I, PI-Mga I, PI-Mga II, PI-Min I, PI-Mma I, PI-Msh I, PI-Msm II, PI-Mth I, PI-Tag I, PI-Thy II CLASSE II which is characterized by: At least one specific motif (GIY-$N_{10/11}$-YIG); and, Cleavage outside the recognition site, leaving 2 nt staggered cut with 3'OH overhangs. Some examples are I-Ncr I, I-Ncr II, I-Pan II, I-Tev I CLASSE III which are chrraracterized by: His-Cys box (SHLC-G-H-C) or no define motif; and, either Cleavage inside the recognition site, leaving 4 nt staggered cut with 3'OH overhangs (One example is I-Ppo I), or Cleavage of long size of staggered cut of at least 10 nucleotides (Some examples are I-Dir I, I-Hmu I, I-Hmu II)

CLASSE IV which is characterized by: Half of the specific motif (GIY-$N_{10/11}$-YIG); and Cleavage outside the recognition site, leaving 2 nt staggered cut with 3'OH overhangs. One example is I-Tev II CLASSE V which is characterized by: HNH motif (HH-G-N-CH-H); and Cleavage inside the recognition site, leaving 2 nt staggered cut, with 5'OH overhangs. One example is I-Tev III.

The meganucleases could also be encoded by "Free" Genes. Up to this date, 5 characterised genes (F-Sce I, F-Sce II (HO), F-Suv I, F-Tev I, F-Tev II) are known in Yeast and bacteriophages.

The meganucleases could be Inteins. Up to this date, 120 protein sequences are characterized (35 with experimental demonstration, 75 theoritical) in 46 different species and strains (7 eukaryotes, 23 bacteria, 16 archaea). There are more than 200 potential sequences.

The endonuclease in the process of the invention can be chosen in the group including in not restrictif title: I-Ceu I, I-Cre I, I-Chu I, I-Csm I, I-Dmo I, I-Pan I, I-Sce I, I-Sce II, I-Sce III, I-Sce IV, F-Sce I, F-Sce II, PI-Aae I, PI-Ape I, PI-Ceu I, PI-Cir I, PI-Ctr I, PI-Dra I, PI-Mav I, PI-Mfl I, PI-Mgo I, PI-Mja I, PI-Mka I, PI-Mle I, PI-Mtu I, PI-MtuH I, PI-Pab III, PI-Pfu I, PI-Pho I, PI-Pko I, PI-Psp I, PI-Rma I, PI-Sce I, PI-Ssp I, PI-Tfu I, PI-Tfu II, PI-Tli I, PI-Tli II, PI-Tsp I, PI-Tsp II, PI-Bsp I, PI-Mch I, PI-Mfa I, PI-Mga I, PI-Mga II, PI-Min I, PI-Mma I, Pi-Msh I, PI-Msm II, PI-Mth I, PI-Tag I, PI-Thy II, I-Ncr I, I-Ncr II, I-Pan II, I-Tev I, I-Ppo I, I-Dir I, I-Hmu I, I-Hmu II, I-Tev II, I-Tev III, F-Sce I, F-Sce II (HO), F-Suv I, F-Tev I, and F-Tev II. Preferably, said endonuclease is chosen from the group consisting of I-Ceu I, I-Cre I, I-Sce I. More preferably, said endonuclease is I-Sce I.

Some endonucleases such as I-Sce I endonuclease could stay non-covalently bound to one half cleavage site after the cleavage (the big site for I-Sce I). This property can be used to protect the free ends of the excised polynucleotide against the exonuclease degradation. Indeed, the cleavage sites are oriented so as the half site having the binding capacity is placed at the extremities of the polynucleotide. Moreover, some restriction endonucleases such as I-Sce I endonuclease further present a NLS-like sequence (Nuclear Localization Sequence) which allows the nucleus targeting. This additional property can be used to facilitate the nuclear targeting of the linearized or excised polynucleotide if the linearization or excision occurs in cytoplasm.

Therefore, in one embodiment of the present invention, the flanking sites are oriented so as the half sites having an endonuclease binding capacity are placed towards the polynucleotide to be linearized or excised. In this embodiment, the free ends of the excised polynucleotide are protected against the exonuclease degradation and/or the transport of the excised polynucleotide to the nucleus is facilitated.

Otherwise, the presence of an endonuclease to the half cleaved site of the excised or linearized polynucleotide masks the free ends and makes these ends less available for recombine with the host cell genome.

Therefore, in an alternative embodiment of the present invention, the flanking sites are oriented so as the half sites having an endonuclease binding capacity are placed towards the vector.

Synthetic endonucleases are also considered in the present invention. These synthetic endonucleases comprise a DNA recognition domain and a DNA cleavage domain.

The DNA recognition domain can be derived from naturally occurring proteins presenting a DNA recognition domain such as the recognition domain of the Type IIS restriction endonuclease (for example amino acids 1–382 of Fokl, U.S. Pat. No. 5,356,802, the disclosure of which being incorporated herein by reference). Suitable recognition domains include, but are not limited to, the recognition domains of zinc finger motifs; homeo domain motifs; POU domains; other DNA binding protein domains of resspressor such as lambda repressor, lac repressor, cro, ga14; DNA binding protein domains of oncogenes such as myc, jun; and other naturally occurring sequence-specific DNA binding proteins that recognize more than 6 base pairs. The DNA recognition domain could comprise the following motifs: helix-turn-helix, zinc finger, steroid receptor, helix-loop-helix, or other helical motif like leucine zipper. The DNA recognition domain is preferably a combination of existing DNA recognition domains if their recognition site is less than 10 nucleotides (WO 96/20951, the disclosure of which being incorporated herein by reference), for example a combination of at least three zinc fingers (U.S. Pat. No. 6,013,453; U.S. Pat. No. 6,007,988, the disclosures of which being incorporated herein by reference). The existing DNA recognition domain can be modified or natural. However, such DNA recognition domain could also be synthetic. The DNA recognition domain could also be a natural or modified polynucleotide.

The DNA cleavage domain can be derived from proteins containing a DNA cleavage domain such as the cleavage domain of the Type II restriction endonuclease (for example, amino acids 383–578 of Fokl, U.S. Pat. No. 5,356,802, the disclosure of which being enclosed herein by reference).

Vector Comprising a Nucleic Acid Encoding the Cleaving Agent, Preferably the Endonuclease The action of the cleaving agent on the host cell can be obtained either by administering to the host cell of the cleaving agent, preferably the endonuclease, or by the expression of the cleaving agent, preferably the endonuclease, in the host cell. In this last case, the process of the invention can be realized by transforming the host cell with a nucleic acid encoding the cleaving agent, preferably the endonuclease, under the control of regulation sequences, notably a promoter adapted to the host cell. An other alternative for the expression of the cleaving agent is the introduction of a mRNA encoding the cleaving agent into the host cell. In the present invention, the vector comprising a nucleic acid encoding the cleaving agent also designates a mRNA encoding the cleaving agent.

The invention also contemplates the use of host cell from a transgenic animal or plant expressing the cleaving agent. In this case, the introduction of the cleaving agent or a nucleic acid encoding the cleaving agent is no more necessary. The nucleic acid encoding the cleaving agent is preferably operably linked ta a promoter specific of the germ line such as VASA, promoters of the protein synthesis in ovocyte, strong promoter with expression as soon as stage II.

The vector comprising a nucleic acid encoding the cleaving agent, preferably an endonuclease, contains all or part of the coding sequence for the endonuclease operably linked to one or more expression control sequences whereby the coding sequence is under the control of transcriptional signals to permit production or synthesis of the endonuclease. Therefore, said nucleic acid encoding said endonuclease is comprised in an expression cassette. More particularly, the vector comprises a replication origin, a promoter operatively linked to said encoding nucleic acid, a ribosome-binding site, an RNA-splicing site (when genomic DNA is used), a polyadenylation site and a transcription termination site. Selection of the promoter will depend upon the desired route for expressing the endonuclease.

Indeed, for an eukaryotic host, the promoter can be a strong promoter such as the metallothionein promoter, an SV40 promoter, a retroviral promoter, the cytomegalovirus (CMV) promoter, an ubiquitus promoter such as villin or actin promoter, a constitutive or inducible promoter, a tissue-specific promoter or tumor-specific promoters such as the α-fetoprotein promoter, the amylase promoter (especially, the murine amylase promoter), the cathepsin E promoter, the M1 muscarinic receptor promoter, or the γ-glutamyl transferase promoter. Optionally, the vector could further contain an enhancer and insulator (Kaffer et al., *Genes Dev.* 2000, 14, 1908–19; EP 859,059; WO96/04390, the disclosures of which are incorporated herein by reference). When the host cell is a fertilized egg or a blastula's cell, the cleaving agent, preferably the endonuclease, needs to be expressed at an early stage.

The elements permitting the production or synthesis of the endonuclease can be native, derived from native elements or manufactured de novo. The elements can then be isolated and fused together by methods known in the art such as using compatible cloning and restriction sites. One advantage of the method according to the present invention is that only a transient expression of the appropriate endonuclease is necessary to excise the linear polynucleotide to be integrated in the host cell genome.

If the host cell is prokaryotic, the vectors of the present invention will thus contain at least one promoter capable of being recognized by a prokaryotic RNA polymerase, and of thus permitting the transcription of a polynucleotide that is operably linked to that promoter. The vector may have multiple prokaryotic promoters if desired. The specific prokaryotic promoter(s) employed will depend upon the prokaryotic cell that is to be the host of the vector. Examples of suitable promoters include constitutive or inducible prokaryotic promoters, such as the λpL or λpR promoters, the T6 polymerase promoter, the T7 polymerase promoter, or other well-characterized promoters (e.g., lac, recA, gal, trp, ara, hut, etc.). Most preferably, the promoter used for expression in prokaryotic cells will be inducible.

The preferred eukarotic expression vectors contain both prokaryotic sequences, to facilitate the propagation of the vector in bacteria, and one or more eukaryotic transcription units that are expressed in eukaryotic cells. The various methods employed in the preparation of plasmids and transformation of host organisms are well known in the art. For other suitable expression systems for both prokaryotic and eukaryotic cells, as well as general recombinant procedures, see Molecular Cloning: A Laboratory Manual, 2nd Ed., ed. by Sambrook, Fritsch and Maniatis (Cold Spring Harbor Laboratory Press: 1989) Chapters 16 and 17; the teaching of which is incorporated herein by reference.

Polynucleotide to be Linearized or Excised Into the Host Cell

The polynucleotide to be linearized or excised with the process of the invention can be any natural or synthetic polynucleotide. Said polynucleotide is preferably exogenous to the host cell. More preferably, said polynucleotide is non-similar to the host cell chromosome sequence. It can comprise a gene sequence or an intergene sequence. It can comprise coding or not coding sequence. Said coding sequence encode any desired product, including peptides, proteins, and RNA. The polynucleotide can encode a reporter protein. It can comprise an encoding sequence for a polypeptide or an antisense, or a regulatory sequence such as a promoter, an enhancer, a silencer, etc . . . It can comprise a recognition sequence for a molecule such as a hormone, a transcriptional factor, an endonuclease, a polynucleotide, etc . . .

The polynucleotide to be integrated can comprise a reporter gene such as β-galactosidase, luciferase, alkaline phosphatase, green fluorescent protein, tyrosinase, DsRed proteins. By reporter gene is intended any nucleic acid encoding a product easily assayed. Preferably, the reporter gene is under the control of a strong promoter or a tissue-specific promoter.

More particularly, the polynucleotide to be integrated with the process of the invention can be chosen in the group including in not restrictif title:

Gene encoding proteins: Secreted proteins such as erythropoietin, albumin, growth hormone, α1-antitripsin; Surface proteins; Otherwise, proteins such as hemoglobin (α, β, γ, ε), collagens (type I, II, III, IV, α1 to 5), chemokine receptors, interferons (α, β, γ), caspase, p53, etc . . .

Sequences coding for Transfert RNA: tRNA for unusual codons (mitochondrial or synthetic tRNA), Sequences coding for Vaccining gene α, a super antigen, an adjuvant (C3d);

Sequences coding for a peptide such as a reduced CMH peptide;

Sequences coding for a HLA chain;

Sequences coding for cytochrome p450 combination;

Sequences coding for a metabolic pathway (lysine or phenylalanine).

Chromatin regulatory sequences such as gene of chromosome X inactivation (gene xist), gene with maternal effect (ddk gene), chromatin opening sequence (HNF4), rich CpG sequence with low or high number of SP1 sites (CCCGCC/G or C/GGCGGG), MAR or SAR sequence, eukoryotic, bacterial or viral chromosomic replication origin;

Transcriptional regulatory sequences such as sequences controlling the chromosome opening for transcription (Locus Control Region LCR, Dominant Control Region DCR), eukaryotic constitutive or tissue specific promoters, inducible promoters (metalloprotein, batcerial operators, T7 promoter, tetracyclin inducible promoter (tet-ON and tet-OFF), enhancers, silencers, RNA polymerase (T7 or viral polymerase), Internal Ribosomal Entry Sites IRES followed by a gene of interest;

Sequences interesting for the genome engineering such as sites of meganucleases (ex: I-Sce I, I-Tev III, F-Sce I, F-Sce II, I-Ceu I, I-Dmo I, I-Chu I, PI-Sce I, PI-PspI or sites for synthetic meganucleases); repeated sequences (ALU, SINES, LINES); micro- and minisatellites; RAG, loxp, FRT or β-resolvase sites; inversed repeat sequences of transposons; transposons; provirus; LTR of transposons and virus;

Antisense sequences and ribozymes: antisense of mRNA, more particularly of p53, Rb, p16, p21 mRNAs, mRNAs of proteins involved in the genome engineering such as meganucleases, RAG, transcriptases, viral mRNAs.

In the case of a gene, the polynucleotide preferably includes all the elements necessary for the expression of the gene. Therefore, the encoding polynucleotode is operably linked to one or more expression control sequences whereby the coding sequence is under the control of transcriptional signals to permit production or synthesis of the encoded product. Said a encoding polynucleotide is comprised in an expression cassette. More particularly, the vector comprises a replication origin, a promoter operatively linked to said encoding nucleic acid, a ribosome-binding site, an RNA-splicing site (when genomic DNA is used), a polyadenylation site and a transcription termination site. Selection of the promoter will depend upon the desired route for expressing the encoded product. Indeed, the promoter can be a strong promoter such as the metallothionein promoter, an SV40 promoter, a retroviral promoter, the cytomegalovirus (CMV) promoter, an ubiquitus promoter such as villin or actin promoter, a constitutive or inducible promoter, a tissue-specific promoter (see WO 98/56902, Table 1; the disclosure of which is incorporated herein by reference) or tumor-specific promoters such as the α-fetoprotein promoter, the amylase promoter (especially, the murine amylase promoter), the cathepsin E promoter, the M1 muscarinic receptor promoter, or the γ-glutamyl transferase promoter. Optionally, the vector could further contain an enhancer and insulator (Kaffer et al., *Genes Dev.* 2000, 14, 1908–19; EP 859,059; WO96/04390, the disclosures of which are incorporated herein by reference).

The elements permitting the production or synthesis of the transgene can be native, derived from native elements or manufactured de novo. The elements can then be isolated and fused together by methods known in the art such as using compatible cloning and restriction sites.

Vector Comprising a Polynucleotide to be Linearized or Excised

The preferred eukarotic expression vectors contain both prokaryotic sequences, to facilitate the propagation of the vector in bacteria, and one or more eukaryotic transcription units that are expressed in eukaryotic cells. The various methods employed in the preparation of plasmids and transformation of host organisms are well known in the art. For other suitable expression systems for both prokaryotic and eukaryotic cells, as well as general recombinant procedures, see Molecular Cloning: A Laboratory Manual, 2nd Ed., ed. by Sambrook, Fritsch and Maniatis (Cold Spring Harbor Laboratory Press: 1989) Chapters 16 and 17; the teaching of which is incorporated herei by reference.

In a preferred embodiment of the invention, the vector comprising the polynucleotide sequence to be linearized or excised also comprises the sequence encoding the cleaving agent, preferably the endonuclease, corresponding to the flanking sites. In this quite preferred embodiment, the gene coding for the cleaving agent, preferably the endonuclease, contains its own sequences of regulation and is not thus placed in the same open reading frame than the polynucleotide to be linearized or excised.

The vector comprising the polynucleotide to be linearized or excised in the host cell genome flanking by the cleaving site can be manufactering according to methods generally known in the art. For example, this vector can be manufactering by chemical synthesis, recombinant DNA/RNA technology or a combination of both (Sambrook et al., Eds., Molecular Cloning: A Laboratory Manual, 2nd edition, Cold Spring Harbor University Press, New York (1989); and Ausubel et al., Eds., Current Protocols In Molecular Biology, John Wiley & Sons, New York (1997); the disclosure of which are incorporated herein by reference)

The vector comprising the polynucleotide to be linearized or excised according to the present invention does not present any free 5' or 3' ends. The vector is advantageously a circular DNA molecule such as a plasmid, but can also be a linear molecule having its ends unaccessible to exonuclease. In a first example, the ends adopt a secondary structure, such as a hairpin, which protects the ends against exonucleolyse. In a second example, the ends could be chemically modified in order to block the exonuclease action. Such modifications can be, for example, the use of phosphothioate links which are resistant to exonuclease (Putney 1981; Olsen and Ecktein 1990). In a third example, the ends could be linked to sterically blocking molecules which impede the access for the exonuclease. Such molecules can be for example a protein or a polyamide. This protein could have some nucleus affinity and could trigger the vector to the nucleus. Preferably, the blocking substituant has a molecular weight of no ore than 1 kD. A variety of non-toxic substituents such as biotin, cholesterol or other steroids, or a non-intercalating cationic fluorescent dye can be used.

Figure 3A:
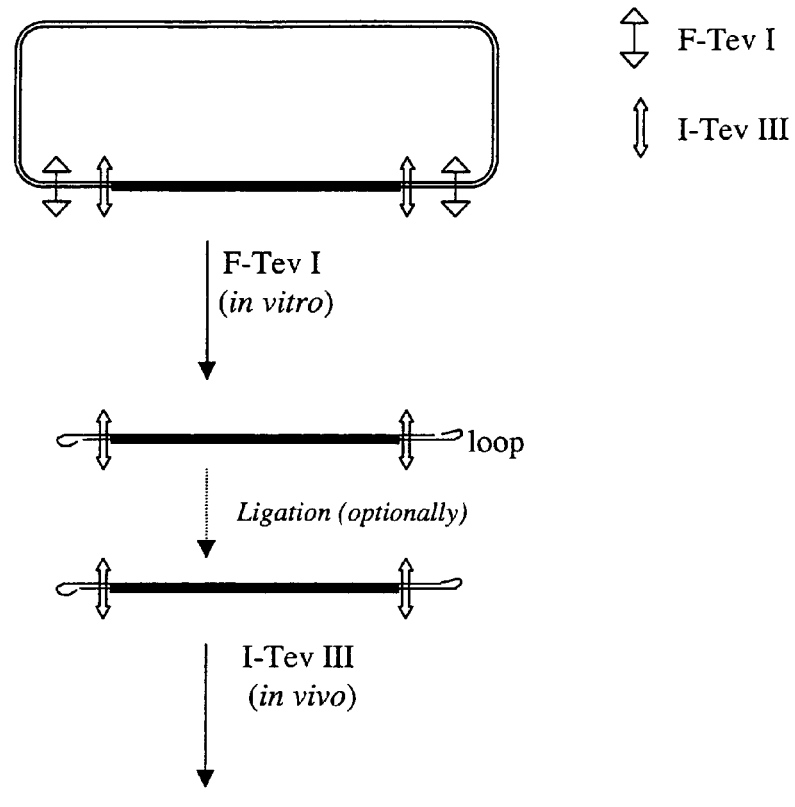
FIG. 3 is a schematic diagram representing some ways for the preparation of linear vector according to the present invention.

The FIG. 3 discloses some examples of linear vectors according to the present invention. In FIG. 3A, a linear vector can be obtained from a plasmid comprising the polynucleotide to be linearized or excised flanked by two endonuclease sites such as I-Tev III sites, themselves flanked by other endonuclease such as F-Tev I sites. In vitro, the F-Tev I endonuclease cleaves the F-Tev I sites and this cleavage produces protruded ends able to adopt a hairpin structure. Optionally, a ligase can be used in order to covalently close the loop. The host cell can be transfected with this linear construct with the hairpins at its ends, the polynucleotide to be linearized or excised being flanked by two endonuclease sites such as I-tev III sites.

Figure 3B:
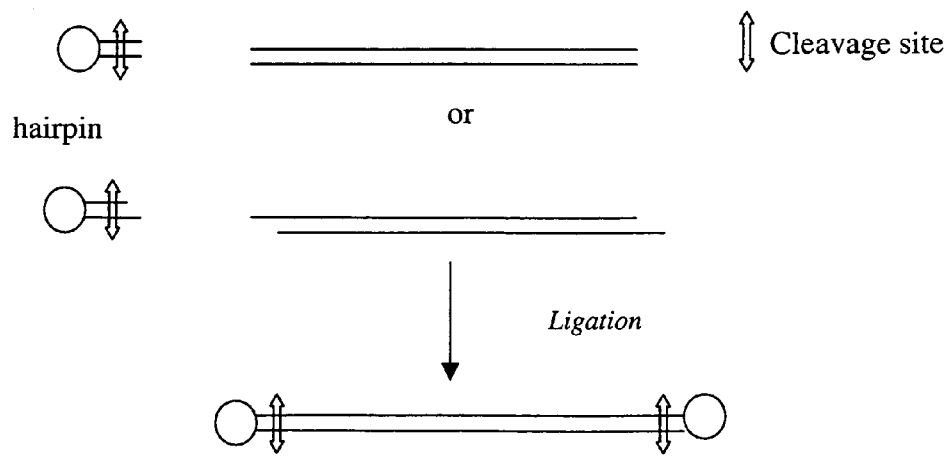

Similarly, in FIG. 3B, a linear vector with a hairpin at each ends can be made as following. In vitro, the polynucleotide to be linearized or excised is prepared with blunt ends or cohesive ends. This polynucleotide is mixed with oligonucleotides forming a hairpin, such hairpin presenting a cleavage site, preferably an endonuclease site, in its tail. The end of the hairpin tail can be blunt or cohesive. A ligation is done in order to covalently link the hairpin and the polynucleotide to be linearized or excised. (Perrin et al, *EMBO J* 1993, 12, 2939–2947; the teaching of which is incorporated herein by reference)

Vectors comprising the polynucleotide to be linearized or excised flanked by the cleavage site and/or, the nucleic acid encoding the cleaving agent, preferably the endonuclease, can be introduced into a cell by a variety of methods (e.g., transformation, transfection, direct uptake, projectile bombardment, using liposomes). Example of suitable methods of transfecting or transforming cells include calcium phosphate precipitation, electroporation, microinjection, infection, lipofection and direct uptake. Such methods are described in more detail, for example, in Sambrook et al., Molecular Cloning: A Laboratory Manual, Second Edition, Cold Spring Harbor University Press, New York (1989); and Ausubel, et al., Current Protocols in Molecular Biology, John Wiley & Sons, New York (1998), the teaching of which is incorporated herein by reference. Other suitable methods are also described in the art. In one embodiment of the present invention, the vectors are associated to the substance susceptible to allow or to facilitate the transformation of the host cell. Vectors comprising the polynucleotide to be linearized or excised flanked by the cleavage site and/or, the nucleic acid encoding the cleaving agent, preferably the endonuclease, can also be introduced into a host cell by targeting the vector to the cell membrane phospholipids. For example, targeting vector to a VSV-G protein, a viral protein with affinity for all cell membrane phospholipids. Such a construct can be produced using methods well known to those practiced in the art.

Cleaving agent, preferably endonuclease can be introduced into a cell according to methods generally known in the art which are appropriate for the particular endonuclease and cell type. For example, an endonuclease can be introduced into a cell by direct uptake, microinjection, calcium phosphate precipitation, electroporation, infection, and lipofection. Such methods are described in more detail, for example, in Sambrook et al., Molecular Cloning: A Laboratory Manual, Second Edition, Cold Spring Harbor University Press, New York (1989); and Ausubel, et al., Current Protocols in Molecular Biology, John Wiley & Sons, New York (1998), the teaching of which is incorporated herein by reference. Other suitable methods are also described in the art. The endonuclease can be coupled to a facilitator of protein entry to facilitate introduction of the enzyme into a cell. Examples of facilitators of protein entry include tat, HSV VP22 and anthrax toxin. Coupling of a protein to a facilitator of protein entry can be accomplished using methods well known to those practiced in the art. Protein delivery strategies (e.g., HSV VP22, anthrax toxin) can be evaluated in accordance with the methods of the invention described herein.

Once in the cell, the vectors comprising the polynucleotide to be linearized or excised flanked by the cleavage site and, if necessary, the nucleic acid encoding the cleaving agent, preferably the endonuclease, or the cleaving agent itself, preferably the endonuclease, are imported or translocated by the cell from the cytoplasm to the nucleus.

Host Cells and Multicellular Organisms

As used herein, a cell refers to a prokaryotic cell such as a bacterial cell or a eukaryotic cell, such as an animal, plant or yeast cell. More preferably, the cell is an eukaryotic cell. The cell can be a stem cell (preferably an embryonic stem cell), a somatic cell, a gamete, a blastomer or an egg (preferably a fertilized egg). The host cell can stem from fish, bird, non-human mammals, insect, amphibian, reptile, preferably from medaka, zebrafish, mice, chicken, xenopus, sheep, cow, rabbit, more preferably from fish, chicken and mice. The host cell can have all stage of differentiation, from totipotent to differenciated cells. Examples of mammalian cells include human (such as HeLa cells), bovine, ovine, porcine, murine (such as embryonic stem cells), rabbit and monkey (such as COS1 cells) cells. The cell may be an embryonic cell, bone marrow stem cell or other progenitor cell. Where the cell is a somatic cell, the cell can be, for example, an epithelial cell, fibroblast, smooth muscle cell, blood cell (including a hematopoietic cell, red blood cell, T-cell, B-cell, etc . . . ), tumor cell, cardiac muscle cell, macrophage, dendritic cell, neuronal cell (e.g., a glial cell or astrocyte, or pathogen-infected cell e.g., those infected by bacteria, viruses, viruseoids, parasites, or prions). Indeed, the method for integrating a polynucleotide in the host cell genome according to the present invention is well adapted for stable transfection.

The process of the invention is thus quite particularly useful for the transgenesis for the gene therapy, production of recombinant protein in animals or plants, production of transgenic animals as models. As a consequence, the invention has for object a method of transgenesis of a pluricellular organism consisting in administering to said organism a composition comprising one or several vector comprising the polynucleotide to be excised or linearized and, optionally the cleaving agent, as defined previously, possibly associated to a substance susceptible to allow or to facilitate the transformation of one or several cellular types of said organism by said vector, then to generate in said cells the linear molecule ready for be integrated by subjecting said cells to the action of the cleaving.

The process of the invention is realized in ovo or in vivo on cells, such as cells in culture, or in situ directly on a multicellular tissue, organ or organism.

The process of transgenesis according to the invention is quite particularly intended for animals chosen in the group including in but not restrictive to: cattle (cows), goats, rabbit, rodents, marmots, monkeys, insects (spider, butterflies, fly), fishes, calmar, amphoxius, xenopus, birds, chickens, ascidies and ovine races (sheeps).

Transgenic fish are produced by introducing a vector according to the present invention into cells of fish, gametes such as spermatozoid or embryonic cell, preferably embryonic cells, and more preferably in a single cell embryo. Where the vector is introduced into embryonic cells, the transgenic fish is obtained by allowing the embryonic cell or cells to develop into a fish. Introduction of the vectors into embryonic fish cells, and subsequent development of the fish, are simplified by the fact that embryos develop outside of the parent fish. Alternatively; when the vector is introduced into spermatozoid, the fecondation of the oocytes is done with the transfected spermatozoid and the embryo is allowing to develop into a fish. Preferably, the spermatozoid is transfected with the vector comprising the transgene and with the cleavaing agent.

Transgenic fish is selected in the group consisting of salmon, trout, tuna, halibut, catfish, zebrafish, medaka, carp, sticklebass, astyanax, tilapia, goldfish, sea bass, sticklebass, astyanax, sturgeon and loach. The most prefered are medaka and zebrafish. However, the method according to the present invention could also be applied for producing aquatic transgenic species such as xenopus, shrimp, sea urchin.

The host cell in the process of the invention can be chosen in the group including in but not restrictive to:

Microorganism:

For industrial production purpose:

*K. lactis, P. pastoris, S. cerevisia, S. pombe, A. immersus, P. limus, E. coli*

2) Bacterial or eukarotic vaccines:

*Listeria monocytognese*, bacille Calmette Guerin

*S. cerevisie, S. pombe, C. albicans, Plasmodium falciparum*, Amoebas

Plants:

1) Biomolecule production

Soya, colza, wheat, corn, rice

2) Transgenic plants

Tomatoes, strawberries, apples, citrus fruits, tobacco

3) Food medecine, and vaccine plants

Spinach, cereal

4) Production of biomaterials

Rubber, paper, wood

Animals:

1) Biomolecules and vaccines production

Cows, goats, sheeps, rabbit, rodents, marmots, monkeys, insects

2) Transgenic animals

Fishes, calmar, amphoxius, xenopus, birds, chickens, cattle, ovine races

3) Biomaterials production

Silkworms, spider, butterflies, fly, sheep, bovine, ovine race

The present invention also relates to the resulting cells and their uses, for example for production of proteins or other genes, biomolecules, biomaterials, transgenic plants, vaccines, transgenic animals or for treatment or prophylaxis of a condition or disorder in an individual (e.g. a human or other mammal vertebrate) arising as a result of a genetic defect. For example, cells can be produced (e.g. ex vivo) by the methods described herein and then introduced into an individual using known methods. Alternatively, cells can be modified in the individual (without being removed from the individual).

Therefore, the invention further relates to a method of production of proteins, biomolecules, biomaterials, transgenic plants, vaccines, transgenic animals or to method of treatment or prophylaxis of a genetic disease in an individual in need thereof, wherein such method comprises the process of in vivo linearisation or excision according to the present invention.

The present invention concerns a method for producing a non-human transgenic animal, wherein embryonic stem cells are tranfected by the method according to the present invention and optionally screened for random integration event, the cells are injected into embryos at a stage at which they are capable of integrating the transfected cells, for example at the blastocyst stage, the embryos are then reimplanted in a surrogate mother, and the chimeric individuals obtained at the end of gestation, and in which colonization by embryonic stem cells of the germ line is observed are mated to obtain transgenic animals.

Furthermore, the invention also concerns a method for producing a non-human transgenic animal, wherein fertilized eggs are tranfected by the method according to the present invention. If necessary, the eggs are reimplanted in a surrogate mother, and the transgenic individuals obtained at the end of gestation. Optionally, the eggs can be screen for randon integration event before the reimplantation in a surrogate mother. Otherwise, the eggs are incubated in condition allowing the growth of the embryo and the generation of the transgenic animal.

For example, fish embryos or embryonic cells can generally be obtained by collecting eggs immediately after they are laid. Depending on the type of fish, it is generally preferred that the eggs be fertilized prior to or at the time of collection. This is preferably accomplished by placing a male ans female fish together in a tank that allows egg collection under conditions that stimulate mating. After collecting eggs, it is preferred that the chorion is removed from the embryo before the embryo exposition for introducing the vectors. This can be done manually or, preferably, by using a protease such as pronase. A fertilized egg prior to the first cell division is considered as one cell embryo. Therefore, the fertilized egg is considered as an embryonic cell. Preferably, a host cell according to the present invention is an embryonic cell of fish, preferably a fertilzed egg or a blastomere from an embryo at the blastula stage. Most preferably, the host cell is a fertilized egg.

Vectors comprising the polynucleotide to be linearized or excised according to the present invention can be introduced into embryonic fish cells using any suitable technique (e.g., transformation, transfection, direct uptake, projectile bombardment, using liposomes). Many techniques for such introduction of exogenous genetic material have been demonstrated in fish and other animals. These include microinjection (Culp, 1991, supra), electroporation (Inoue et al., 1990, *Cell. Differ. Develop.* 29, 123–128; Müller et al. 1993, *FEBS Lett.* 324, 27–32; Murakami et al. *J Biotechnol.* 34, 35–42; Müller et al. 1992, *Mol. Mar. Biol. Biotechnol.* 1, 276–281; Symonds et al. 1994, *Aquaculture* 119, 313–327), particle gun bombardment (Zelennin et al., 1991 *FEBS Lett.* 287, 118–120), and the use of liposomes (Szelei et al., 1994, *Transgenic Res.* 3, 116–119) (the teaching of these documents is incorporated herein by reference). Preferably, the vectors are introduced by microinjection.

Cleaving agent, preferably endonuclease can be introduced into an embryonic fish cell according to methods generally known in the art which are appropriate for the particular endonuclease and cell type. Preferably, the cleaving agent is co-injected with the vector comprising the transgene.

After introduction of the vector(s) according to the present invention, the embryo is allowed to develop into fish. This generally involves no more than incubating the embryos under the same conditions used for incubating egg. However, the embryonic cells can be also be briefly incubated in an isotonic buffer. If appropriate, expression of the transgene can be observed during the embryo development.

Fish or fish embryo harboring the transgene can be identified by any suitable means. For example, the fish genome can be probed for the presence of the transgene by Southern or Nothern blotting. The presence of the transgene can also be detected using PCR or other sequence-specific nucleic acid amplification techniques. In order to identify the expression product of the transgene, the presence of this product can be assayed.

The transgenic fish can provide a fish with the desired characteristic such that the fish or a descendent of the fish has that desired characteristic. Examples of a desired characteristic include enhanced and/or novel nutritional value, disease resistance, growth enhancement (faster growth, increased body size or increased litter size) or production of a desired protein. By desired protein is meant a protein that bestows a desired trait on the fish in which it is produced or a protein which when isolated from the fish is desirable for uses outside of the fish. The desired protein may be produced in a specific tissue, a subset of tissues or in wide range of tissues. Examples of desired proteins include proteins which correct an abnormal condition in the fish or therapeutic proteins for the fish or some other animal.

Transgenic fish can be used as study model. The pattern of expression of a gene, more particularly a fish gene can be study with such transgenic fish by measuring or identifying expression of the transgene in different tissue (tissue-specific expression), at different times during development (developmentally regulated expression or developmental stage-specific expression), in different cell lineages (cell lineage-specific expression). Transgenic fishes are also useful for identifying compounds or genes that affect the expression of a gene which has been introduced by transgenesis, preferably a fish gene. One way to analyze the expression in the different fish tissue is to dissect the fish and assay in the separate tissue sample. RNA can be detected using any of numerous nucleic acid detection techniques. The use of reporter proteins is preferred since these proteins are easily detected. A preferred way of assaying the expression pattern of the transgene during the development is to use an expression product that can be detected in living embryos or animals such as GFP or DsRed.

In one application of the present invention, introduction of the transgene can create an insertional mutation in the fish. Such mutated genes are easely cloned because the inserted transgene serves as a tag for cloning. Genes affecting any process of interest that can be detected can be identified by such insertional mutagenesis. Moreover, in another application, the transgene is a reporter gene used in a gene trap construct. By gene trap is meant a reporter gene that can only be expressed after the DNA integrates into an active gene in the host cell, in this case a fish cell. Gene trap vectors are particularly useful for identifying insertions into active genes. (Kitajima et al., *Biochem Cell Biol* 1998 76:1029–37; Zambrowicz et al, *Int J Dev Biol* 1998 42 1025–36; Cecconi et al, *FEBS Lett.* 2000 480 63–71; the teaching of these documents are incorporated herein by reference)

The process of the invention is thus quite particularly useful for the production of recombinant protein fish, production of transgenic fishes as models. As a consequence, the invention has for object a method of fish transgenesis consisting in administering to said embryonic fish cell a composition comprising one or several vector comprising the polynucleotide to be excised and, optionally the cleaving agent, as defined previously, possibly associated to a substance susceptible to allow or to facilitate the transformation of one or several cellular types of said organism by said vector, then to generate in said cells the linear molecule ready for be integrated by subjecting said cells to the action of the cleaving.

The present invention also relates to the resulting cells and their uses, for example for production of transgenic fish as model or food, or for producing proteins or other genes, biomolecules, biomaterials, and vaccines.

Therefore, the invention further relates to a method of production of proteins, biomolecules, biomaterials, transgenic plants, vaccines, transgenic fish, wherein such method comprises the process of in vivo or in ovo linearisation or excision according to the present invention.

Furthermore, the invention also concerns a method for producing a transgenic fish, wherein fertilized eggs are tranfected by the method according to the present invention and the eggs are incubating in conditions allowing its development in transgenic fish. Optionally, the eggs can be screen for randon integration event before their incubation.

The informations detailed for the fish are applicable to the non mammalian species such as xenopus, shrimp, sea urchin, acsidies, birds, chicken, amphoxius.

The invention also contemplates a method of transgenesis in which a complete genetic material (the DNA contained in a nucleus) is transferred together with the vector comprising the polynucleotide to be integrated in the host genome and the cleaving agent in an unfertilized egg whose own nucleus has been removed.

The invention still has thus for object a pharmaceutical composition comprising as active agent a vector comprising the polynucleotide to be linearized or excised according to the present invention, possibly associated in the pharmaceutical composition to a substance susceptible to allow or to facilitate the transformation of one or several cellular types by said vector. One embodiment of the pharmaceutical composition according to the invention consists in associating said composition in a transgenesis kit with a composition containing the cleaving agent, preferably a restriction endonuclease.

The invention has finally for object the use of a vector comprising the polynucleotide to be linearized or excised according to the present invention, for the preparation of a pharmaceutical composition intended to transform one or several cellular types of a subject in which said composition is administrated, said cells being exposed after transformation to the action of the cleaving agent, preferably a restriction endonuclease. As indicated previously said vector is possibly associated in the pharmaceutical composition according to the invention to a substance susceptible to allow or to facilitate the transformation of one or several cellular types by said molecule.

The invention concerns a method of treating or prophylaxis of a genetic disease in an individual in need thereof by random integration of a polynucleotide into the individual genome according to the present invention. A genetic disease is often due to a low expression of a gene or by the expression of a mutated gene which is not functional. For example, by the integration of a correct gene with the appropriate elements for its expression, the gene can be expressed and the genetic defect can be compensated. In case of a genetic disease due to an overexpression of a gene, the integration of a polynucleotide allowing the expression of an antisense, for example, could impede the expression of this gene and compensate the genetic defect due to the overexpression. The method according to the present invention can be applied to any one of contemplated gene therapy.

Other advantages and characteristics of the invention will appear in the following examples

EXAMPLES

Example 1

Figure 5:
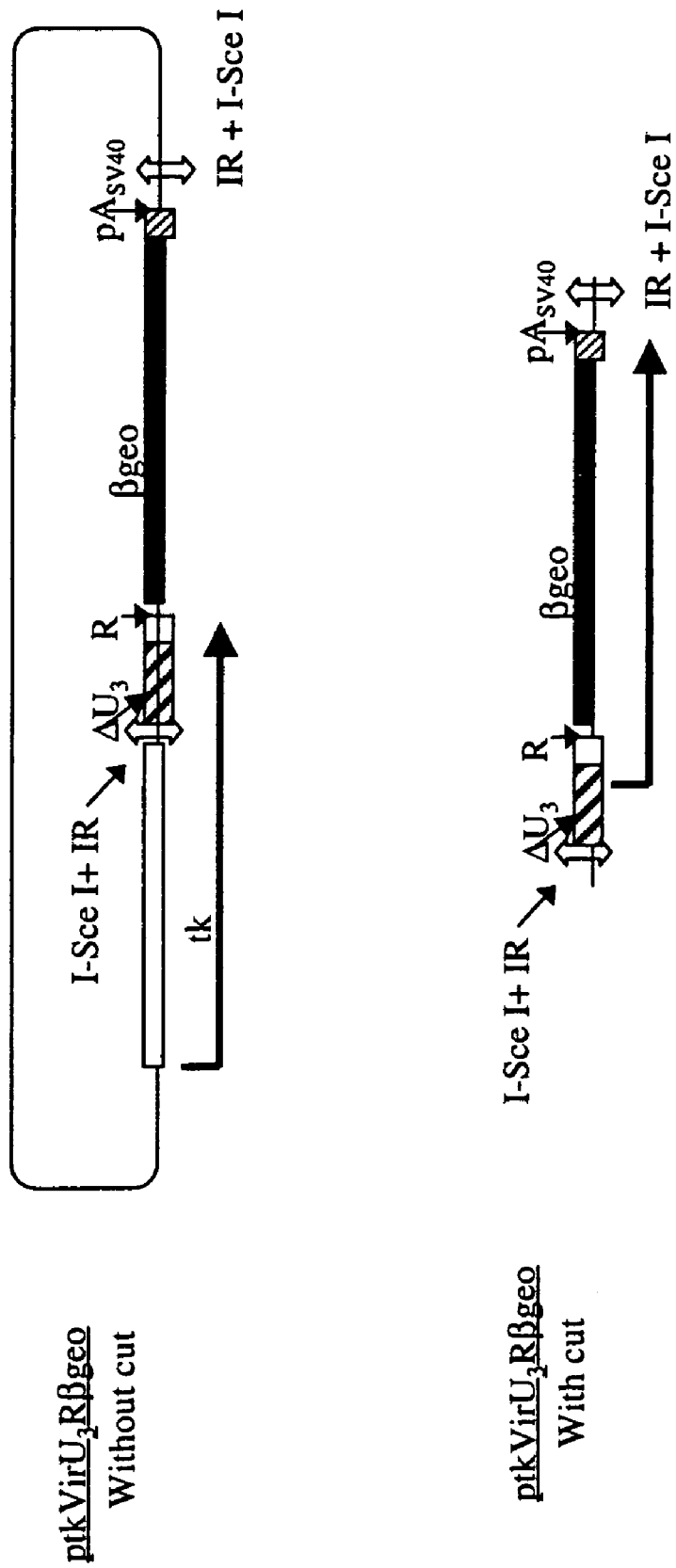
FIG. 5 is a schematic diagram disclosing the validation system used in Example 1. "I-Sce I", "IR", "pA$_{SV40}$" respectively refer to I-Sce I endonuclease recognition and cleavage site, invert repeat, and the polyadenylation signal of SV40.

Method of in Vivo Linearization in Human Cells (See FIGS. 4 and 5)
Construction of pVirtkU$_3$R☐geo (see FIG. 4)

pU$_3$R plasmid was obtained by the insertion in pBS KS+plasmid (Stratagene, #X52328) of the 990 bp fragment from the segment 7840–8330 of the murine leukemia Moloney virus (MoMULV) comprising the U$_3$ sequence from the 3' Invert Repeat sequence following by the R sequence. The U$_3$R fragment comprised the enhancer and promoter sequences of MoMULV and the polyadenylation signal AATAAA contained in the R sequence. The pVirU$_3$R plasmid was obtained in two steps. Firstly, the sequence 5'-ATTACCCTGTTATCCCTAATGAAAGA-3' (SEQ ID NO:1) comprising the recognition and cleavage site of the I-Sce I endonuclease followed by the Invert Repeat of MoMULV virus was inserted upstream of the U$_3$R sequence of the pU$_3$R plasmid. This I-Sce I endonuclease site is called in this example "5' I-Sce I endonuclease site". Secondly, the sequence 5'-TAGGGATAACAGGGTAATTTACTTTCA-3' (SEQ ID NO:2) comprising the Invert repeat of MoMULV virus followed by the recognition and cleavage site of the I-Sce I endonuclease was inserted downstream of the U$_3$R sequence of the intermediate plasmid. This I-Sce I endonuclease site is called in this example "3'I-Sce I endonuclease site". The orientation of the I-Sce I endonuclease sites was done so as to keep the small site (TAGGGAT or ATCCCAT) towards the U$_3$R sequence. Therefore, the site orientation was opposite in order to avoid the generation of cohesive ends. This orientation is called "the small site towards the insert center". pVirU$_3$R☐geo plasmid was obtained by the insertion in the plasmid pVirU$_3$R of a 5,3 kb Xho I restriction fragment comprising the fusion gene ☐geo from pRSV☐geo plasmid (Friedrich and Soriano, 1991, *Genes Dev*, 5, 1513–1523; the disclosure of which is incorporated herein by reference) (lacZ gene fusion, encoding the bacterial β-galactosidase gene fused in phase at its 3' end with the neo resistance gene encoding the neomycine phosphotransferase) following by the polyadenylation site of SV40 virus at the Xho I site located between the R sequence and the Invert Repeat of "3' I-Sce I endonuclease site". In the pVirU₃R☐geo plasmid, the ☐geo expression was controled by U₃ promoter of MoMULV. The SV40 polyadenylation site is directed towards the "3' I-Sce I endonuclease site". The pVirtkU₃R☐geo plasmid was obtained by the insertion in pVirU₃R☐geo upstream of the "5' I-Sce I endonuclease site" of 2.5 kb BamHI-NsiI restriction fragment of pHSVTK plasmid (Mansour et al, 1988, *Nature*, 336, 348–352; the disclosure of which is incorporated herein by reference) comprising a gene encoding the thymidine kinase (tk) of Herpes simplex virus HHV1 under the control of its own promoter and without its polyadenylation site. The expression of the tk gene uses the polyadenylation site of the MoMULV virus R sequence. See FIG. 4

Use of pVirtkU₃Rβgeo System for the Validation of the in Vivo Linearization Method pVirtkU₃Rβgeo was cotransfected in the target organism with the I-Sce I endonuclease expression vector pCMV-I Sce I+ or pCMV-I Sce I− (Choulika et al, 1995 *Mol Cel Biol*, 15, 1968–1973; the disclosure of which is incorporated herein by reference). pCMVI-SceI+ is a vector in which the ORF encoding the endonuclease has a good orientation relative to the CMV promoter for the expression of I-Sce I endonuclease. pCMVI-SceI− refers to a plasmid construct in which the ORF encoding the endonuclease has a reverse orientation relative the CMV promoter and, therefore, does not lead to the endonuclease expression.

If pVirtkU₃Rβgeo plasmid was cleaved in vivo by I Sce I endonuclease, the cleavage occurred upstream and downstream of the Invert Repeat sites, namely at the recognition and cleavage sites of the I-Sce I endonuclease. If pVirtkU₃Rβgeo plasmid was cleaved in vivo by I-Sce I, the MoMULV promoter contained by U₃ activated the βgeo gene transcription. If pVirtkU₃Rβgeo plasmid was not cleaved, the transcription of the cistron expressing tk gene ended by the polyadenylation in the R sequence located downstream of U3 and prevented the βgeo expression. The integration selection of the in vivo linearized fragment was done either in two steps or only one step. In two steps selection; firstly, a selection with 1 μM of ganciclovir in order to eliminate clones presenting an integration of the whole plasmid; and secondly, a selection with 50 μg/ml of G418 in order to select the clones expressing βgeo. In one step selection, a selection with 50 μg/ml of G418 in order to select the clones expressing βgeo. See FIG. 5.

Construction of pU₃Rβgeo Control Plasmid pU₃Rβgeo plasmid was obtained by the insertion in pU₃R of a 5.3 kb Xho I restriction fragment comprising the fusion gene β-geo from pRSVβgeo plasmid (Friedrich and Soriano, supra) following by the polyadenylation site of SV40 virus at the Xho I site located downstream the R sequence. In the pU₃Rβgeo plasmid, the βgeo expression was controled by U₃ promoter of MoMULV. The SV40 polyadenylation site is directed towards the 3' I-Sce I endonuclease site. See FIG. 4.

Preparation of the Linear Fragment U₃Rβgeo as Linear Control

The linear U₃Rβgeo fragment was isolated after digestion of 10 μg of ptkU₃Rβgeo plasmid by Xba I and Not I by electrophoresis on 0.8% agarose gel with TAE 1X. A 9.7 kb fragment was isolated and purified on glass beads with Gene-Clean II's protocol. The purified U₃Rβgeo fragment was resuspended in H₂O pH 7 for transfection. See FIG. 4.

Transfection Protocol of Human 293T Cell 20 h before transfection, 293T cells were seeded at a density of 5×10⁴ cells per 35-mm dish on DMEM (Dulbecco Modified eagle Medium) medium with 10% inactivated foetal veal serum (SVFi). Cells are incubated in an incubator of 1 atm, 5% CO₂, 100% humidity, 37° C. The transfection was done by phosphate calcium precipitation with a mixture of 125 mM CaCl₂, NaCl 8.18% (WN), HEPES 5.94%, Na₂HPO₄ 0.2% pH 7.12 at 25° C. in presence of 2 μg DNA. Precipitates were maintained 16 h on cells. Then, the culture medium with the precipitate was replaced by fresh DMEM 10% SVFi medium.

48 h after transfection, cells were fixed in a paraformaldehyde 4% solution during 5 min at 25° C. Cells were washed twice in PBS×1 (Phosphate buffer saline). Then cells were placed in X Gal coloration medium during 24 h at 37° C. for hystochemical staining by β-galactosidase expression of βgeo gene. Otherwise, cells were placed in selection medium DMEM 10% SVFi with 60 μg/ml of G418. The selection medium was changed by new one every 48 h. The selection was maintained during 15 days until the emergence of isolated cellular clones. These clones were isolated on plates of 24 wells of 1 cm diameter, and were amplified in order to be freezed and analyzed.

Results of Transfection of 293T Cells by pVirtkU₃Rβgeo

2 μg of DNA mixture (pVirtkU₃Rβgeo+pCMV-1 Sce I) were transfected at a density 5×10⁴ cells per 35-mm dish with the following ratios and in presence of the following transfection controls which are disclosed in Table 1.

TABLE 1

35 mm-dish were transfected by DNA concentration and in mixture according to the table. Each assay was done four times, two times for histochemical staining and two times for clonal selection. Each # number corresponds to a transfection mixture, columns which indicates the plasmid constructs used in the mixture.

| ADN/Transfection Number | pCMVI-SceI+ | pCMVI-SceI− | pVirtkU₃Rβgeo | pU₃Rβgeo | U₃Rβgeo |
|---|---|---|---|---|---|
| #1.0 | 0,5 μg | — | 1,5 μg | — | — |
| #1.1 | — | 0,5 μg | 1,5 μg | — | — |
| #2.0 | 0,5 μg | — | — | 1,5 μg | — |
| #2.1 | — | 0,5 μg | — | 1,5 μg | — |
| #3.0 | — | — | — | — | 1,5 μg |
| #3.1 | 0,5 μg | — | — | — | 1,5 μg |
| #3.2 | — | 0,5 μg | — | — | 1,5 μg |

48 h after transfection, cells were fixed and β-galactosidase expression was revelated by histochemical staining. Clones showing β-galactosidase expression (β-gal clones) were counted (see Table 2). Furthermore, cells were selectionned on a culture medium comprising 60 μg/ml of G418. Cell culture medium were changed by fresh medium each 48 h of incubation. After 15 days of post-transfection, clones resistant to G418 were isolated and amplified (see Table 2).

TABLE 2

Results of 293T transfection by the mixtures according to Table 1.

| Transfection number # | 1.0 | 1.1 | 2.0 | 2.1 | 3.0 | 3.1 | 3.2 |
|---|---|---|---|---|---|---|---|
| X-gal | | | | | | | |
| Cells +/dish | 38454 | 10742 | 11023 | 10908 | 7439 | 8243 | 8899 |
| Clones +/dish | 10751 | 2684 | 2536 | 2923 | 2613 | 2522 | 2866 |
| G418 | | | | | | | |
| Clones/dish | 74 | 6 | 3 | 9 | 2 | 2 | 3 |

Results show a significant increase of the construct integration for Transfection number 1.0. This transfection number corresponds to the transfection of a plasmid comprising the polynucleotide to be integrated, namely $U_3R$-βgeo-polyA$_{SV40}$, flanked by two I-Sce I endonuclease sites with a plasmid comprising an expression cassette for I-Sce I endonuclease. The integration of the plasmid with in vivo linearization was about 4 to 10 times more effective than the linear fragment $U_3R$βgeo.

Genomic DNA of the isolated clones was extracted and analyzed by Southern hybridization (digestion of genomic DNA with EcoR V) with probes comprising a restriction fragment EcoRI of 3 kb containing lacZ gene from plasmid pGemnlslacZ (pGem vector from Promega in which has been inserted the lacZ gene and a nuclear localization sequence). See FIG. 6. Southern analysis showed that the integration is unique and not in tandem. Indeed, a tandem integration would show a 2,6 kb band which was never seen. Sometimes, like in line 12, several integration events occurred. Therefore, the in vivo linearization method makes the integration unique.

Some experiments were done with a cotransfection with a plasmid expressing an integrase (+IN). The integrase used in this experiment is the active fragment of the MoMULV virus. Indeed, the nucleic acid encoding the active fragment has been cloned in an expression vector. The integration showed an increase of about 6 times compared with the in vivo linearization method without any integrase. Therefore, optionally the method for integrating a polynucleotide into the host cell genome according to the invention also comprises the introduction into host cell of integrase itself or a nucleic acid encoding integrase.

The integration site of the integrated constructs in 24 different isolated clones was cloned by reverse PCR and analyzed by sequencing. The junctions between the integrated constructs and the genomic DNA were caracterized. These junctions showed that the integrity of the polynucleotide to be integrated is conserved and that the insertion is unique.

Example 2

Method of In Vivo Linearization in COS Cells

Construction of ppSV40NeoIRESegfp Plasmids

The ppSV40NeoIRESegfp intermediate plasmid was obtained in two steps. First, the cassette containing the Simian virus 40 promoter (pSV40) and the neo resistance gene encoding the neomycin phopshotransferase was excised from the pcDNA3.1+ plasmid (Clonetech, Palo Alto, Calif., USA) and cloned in the pIRES2-EGFP plasmid (Clonetech, Palo Alto, Calif., USA) at the SmaI site, resulting in the insertion of the pSV40-Neo cassette upstream of the IRES bicistronic element and EGFP gene. Second, the PyTknlslacz cassette from the pPytknlslacz plasmid (Henry et al., *C. R. Acad. Sci. III,* 322(12): 1061–1070 (1999)) was excised and replaced by the entire pSV40-Neo-IRES-EGFP (ppSNIE) cassette and was inserted before the SV40 polyA site.

From this initial construct, a plasmid was derived by inserting the sequence corresponding to the I-SceI cleavage site both upstream of the SV40 promoter (5') and downstream of the SV40 polyA site (3').

Transfection Protocol of COS Cells

A day before transfection, 5×10$^4$ COS cells were seeded in 6-well plate in DMEM (Dulbecco's Modified Eagle Media) media supplemented with 10% Fetal Calf Serum, 2 mM L-Glutamine and incubated at 37° C. in a 7% $CO_2$ atmosphere. The transfection was done by the Effectene method (Qiagen, Chatsworth, Calif., USA). The transfection protocol has been set up according to the manufacturer recommendations. Briefly, 1 μg of plasmid DNA was diluted in 100 μl DNA-condensation buffer in the presence of Enhancer reagent (ratio DNA/Enhancer is 1/8). After a 5 min. incubation period, 10 μl of Effectene is added to the DNA (ratio DNA/Effectene is 1/10). The mix is vortexed and incubated for 10 min. at room temperature. 600 μl of complete media is then added to the DNA/Effectene complexe, mixed and sprinkled over cells. Cells are washed the next day and incubated for a total period of 48 h at 37° C., 7% $CO_2$.

A FACS™ analysis is performed on an aliquot of the transfected cells using a FACscan flow cytometer and CellQuest software (Becton-Dickinson, Franklin Lakes, N.J., USA). The remaining cells are plated on a 10 cm dish and selection media containing G418 (Life Technologies, ) at the concentration of 400 μg/ml is added. Alternatively, cells were resuspended at the density of 2000 cells/ml and 100 μl of suspension were seeded in 96-well plates. After 3 weeks, resistant clones were isolated and amplified in 24-well plates for further analysis.

Genomic DNA Extraction, Quantitation and Southern Blot Hybridization.

Genomic DNA was extracted from cultured cells using the High Pure DNA Prep Kit (Roche, Mannheim, Germany) and was quantified using the Picogreen™ dsDNA quantitation Kit (Molecular Probes, Eugene, ON, USA) according to manufacturers' protocols.

1 μg of genomic DNA from independent clones was digested with HindIII restriction enzyme (NEB, Beverly, Mass., USA). After DNA electrophoresis and blotting on Hybond-N+ membranes (Amersham, Pisscataway, N.J., USA), blots were probed with the NEO probe using a non-radioactive DIG based nucleic acid detection protocol (Roche, Mannheim, Germany).

Results of Transfection of COS Cells by ppSNIE Plasmids ppSNIE plasmid was co-transfected with the I-SceI endonuclease expression vector pCMV-I-SceI+ (Choulika et al, 1995 *Mol Cel Biol,* 15, 1968–1973). As negative controls, ppSNIE plasmid was cotransfected with pCMV-I-SceI– in which the ORF encoding the endonuclease has a reverse orientation and, therefore, does not allow the I-SceI expression. 1 μg of DNA mixture (0.5 μg of ppSNIE plasmid +0.5 μg pCMV-I-SceI–) or (0.5 μg of ppSNIE plasmid+0.5 μg pCMV-I-SceI+) were used to transfect 5×10$^4$ cells in 6-well plates. 48 h post-transfection, cells were harvested and analyzed by flow cytometry. Reproducibly, transfection rate of COS cells was between 35 and 45% of GFP+ cells. Thus, co-transfection of ppSNIE plasmid with I-SceI expression (pCMV-I-SceI+) or control (pCMV-I-SceI–) vectors did not affect the transient expression of EGFP reporter.

Remaining cells were plated on 10 cm dishes and selecting media was added. Three weeks later, resistant clones were isolated and amplified. Genomic DNA from independent clones was extracted and analyzed by Southern hybridization. 0.5 μg of genomic DNAs were digested with HindIII restriction enzyme, separated on agarose gel and transferred on nylon membrane. Blot was then probed with the Neo probe.

The results were shown with a Southern Blot analysis. As expected, all but clones #3 and #26 showed a 1.5 kb band corresponding to the HindIII fragment within the ppSNIE cassette. The intensity of the 1.5 kb band is highly variable in clones from I-SceI– co-transfection with the presence of huge concatemers (see clones #5, 6, 8 and in a lesser extent clones #11, 15, 16). In contrast, bands in clones from I-SceI+ co-transfection are less intense suggesting the presence of a few copy number.

Example 3

In ovo Linearization by the I-SceI Meganuclease Boosts Transgene Integration in Fish Eggs.

Circular plasmidic DNA, bearing a muscle specific promoter followed by a GFP reporter gene and flanked by two I-Sce I recognition sites, was injected in one-cell stage fish embryos. When this construct was co-injected with the I-Sce I meganuclease in a magnesium free buffer (so that the enzyme remains inactive extracellularly), the expected GFP muscular expression was spectacularly improved (80% of the embryos exhibited strong fluorescence in the trunk musculature, as compared to 20% when the injections were performed without the meganuclease). Even more striking was the dramatic increase in germline transmission. Whereas in classical egg injection experiments, it does not, in most cases, exceed a few percents, due to late chimeric integrations, the frequency of germline transmission in fish co-injected with the meganuclease was boosted to 50%, suggesting that a single insertion occurred at one-cell stage of the founder fish. Further Southern analysis confirmed that single low copy integrations occurred in most cases. To assay whether early integration events may be due to in vivo cleavage of DNA, and not to its targeting to the nucleus by the meganuclease, control constructs bearing deleted or mutated recognition sites (bound, but not cleaved, by the I-Sce I meganuclease) were injected with the meganuclease. We propose that meganuclease-induced in ovo linearisation, by limiting degradation of preintegrative DNA free ends, is a simple and efficient process to improve transgenesis by egg injection.

This example shows that meganuclease-mediated transgenesis is indeed a very simple technique that is spectacularly more efficient than the other methods currently reported in fish.

Materials and Methods
Plasmid Constructs

The pαact-GFPM2 was constructed with two I-SceI recognition sequences in a 7, 8 kb plasmid bearing an EGFP reporter gene driven by an α-actin muscle specific promoter (pαact-GFP, gift of Dr. Higashijima). Briefly, two subcloning steps were used to insert <<megalinkers>> at the Eco RI and KpnI sites, located on both sides of the α-actin/ GFP/polyA cassette in the Bluescript polylinker. Megalinkers were generated by annealing complementary oligonucleotides containing the I-SceI recognition site (CCGCTAGGGATAACAGGGTAATATA (SEQ ID NO:3)) flanked by free ends compatible with either of the EcoRI or KpnI digest products. After ligation of the megalinker with the linearized plasmid, DNA was digested again by the enzyme used to linearize the plasmid and transformed by heat pulse into XL1 Blue ultra-competent $E.$ $coli$ (Stratagene). Clones were sequenced to determine the orientation of the non-palindromic I-SceI site.

Several other constructs were obtained by inserting different linkers at the KpnI site: pαact-GFPM with only one I-SceI recognition site, pαact-GFPDM with a shortened recognition site (GGGTAATATA (SEQ ID NO:4)), and pαact-GFPMM containing a mutated (TAGGGtTAA-CAGGGTAAT (SEQ ID NO:5)) version of the I-SceI site.

These later two sites bind the meganuclease but are not cleaved efficiently [Colleaux, 1986; Colleaux, 1988].

Microinjection of Plasmid DNA with Meganuclease

Medaka embryos and adults of an Orange-Red strain (kindly provided by A. Shima, Tokyo University, Japan and Y. Ishikawa, Chiba, Japan) were used in all experiments. Fish were raised in 20 liter tanks at 26° C. Adults were placed under a reproduction regime (14 h light/10 h dark). Eggs were collected immediately after spawning (at the onset of light), cleaned and placed in Yamamoto's embryo rearing medium [Yamamoto, 1975]. For injection, one-cell stage embryos with a recently formed blastodisc were selected [Iwamatsu; 1994], and transferred at 4° C. to stop development. Approximately ten embryos at a time were positioned, cytoplasmic discs to the top, in agarose slots made with a plastic mold as described in [Westerfield; 1993]. In all experiments, an Olympus SZX12 stereomicroscope equipped with a micromanipulator MM3 (Fine Science Tools, Germany) and a pressure injector (FemtoJet, Eppendorf, Germany) were used. Borosillicate glass capillaries (1 mm outer diameter, GC100T, Clark Electromedical Instruments, UK) were pulled using a vertical puller (PC-10, Narashige, Japan). Capillaries were backfilled with the injection solution (DNA: 10 µg/ml; meganuclease buffer (Roche Diagnostic, Germany): 0,5×; meganuclease I-SceI: 1 unit/µl; 0,1% phenol red) using sterile microloaders (Femtotips, Eppendorf, Germany). Immediately before injection, the micropipettes tips were broken to about one micrometer in diameter with fine forceps. DNA was injected through the chorion by inserting the pipette directly into the thin blastodisc. One pressure pulse resulted in the injection of a droplet (estimated volume 300 pl) visualised by the phenol red. Embryos were then removed from agarose and placed in Petri dishes at 26° C. GFP expression was first screened at three days after injection. Embryos were then raised to sexual maturity and pair-wise crosses were done to identify fish that had transmitted the transgene to their progeny.

Southern Blot Analysis

For southern blotting, genomic DNA from F1 fish was extracted using proteinase K and phenol [Sambrook and Russel; 2001]. To get enough DNA, whole one month old fish were used. To avoid DNAses, muscles from older fish were dissected out for DNA extraction. DNA was digested to completion with BamHI, EcoRI, XbaI, XhoI. DNA standards were prepared by digesting the pαact-GFP plasmid by the corresponding enzymes. Using an estimated DNA content of $10^9$ bp per haploid genome, 50 pg of digested pαact-GFP plasmid were loaded. Samples (10 □g per lane) were electrophoresed in 0,9% agarose in 1×TBE and blotted onto a nylon Zetaprobe membrane (Biorad) by upward capillary transfer, as recommended by the Zetaprobe manufacturer. Filters were hybridized in a roller bottle overnight at 65° C. with random-primed radiolabeled probes (XhoI/ EcoRV fragment) corresponding to αactin/GFP/polyA.

Epifluorescence Microscopy

Embryos were observed and scored using a MZFLIII Leica dissecting microscope using a 370 to 420 nm excitation filter and a 455 nm LP emission filter. Photographs were acquired using a Nikon DXM1200 digital camera. For photography, embryos were dechorionated with hatching enzyme [Yasumasu; 1994], following the procedure described in [Wakamatsu; 1993] and placed in 80% glycerol in PBS or in Vectashield mounting medium.

Results

Transient expression of GFP in muscles of injected embryos is improved when the meganuclease is co-injected with the construct Circular plasmid DNA, bearing the pαact-GFPM2 actin promoter followed by a GFP reporter gene and flanked by two I-SceI recognition sites (pαact-GFPM2) was first tested for expression by injecting it in one-cell stage embryos (stage 2a, [Iwamatsu; 1994]). The DNA concentration (13 ng/μl) was chosen as the highest one which did not lead to a significant mortality of the injected eggs.

GFP reporter gene expression in the embryos was examined at a number of distinct developmental stages using fluorescence binocular microscopy. Onset of GFP expression was first observed in a few embryos after two days (stage x).

Generally, embryos were scored after three days of development when the muscular α-actin GFP expression was well underway. The embryos were grouped according to the intensity of fluorescence, in order to quantitatively estimate the level and distribution of transgene expression in each experiment.

About 50 percent of the embryos showed no muscular fluorescence and were classified as negative (N). In the other embryos, the number of GFP positive cells ranged from a few cells (classified as weak, W), to almost an almost ubiquitous muscle cells labelling (strong, S). When the expression was detected in a large domain of the tail, but nowhere else, the expression was qualified as moderate (M). Expression in individual muscle cells was always strong enough to be easily detectable, and no ectopic expression was observed.

When pαact-GFPM2 was linearized in vitro with I-SceI, purified from an agarose gel and injected in the same conditions as reported above, results were similar to those obtained with circular pαact-GFPM2.

When pαact-GFPM2 was co-injected with the commercially available I-SceI meganuclease in a magnesium free buffer (so that the enzyme remains inactive extracellularly), the GFP muscular expression was spectacularly improved. About 80% of the embryos exhibited a moderate or strong expression in the trunk musculature, as compared to 20% when the injection was performed without the enzyme.

Thus, transitory transgene expression in F0 fish was readily and efficiently improved by the meganuclease protocol, by a mechanism that presumably involves an in vivo linearisation step of the injected circular plasmid.

Improvement in F0 Transgene Expression is Linked to in ovo Linearisation

I-SceI meganuclease was known to have some NLS activity. To assess whether early integration events were indeed due to an in vivo cleavage of DNA, and not to its targeting to the nucleus by the meganuclease, control constructs bearing deleted (pαact-GFPDM) or mutated (pαact-GFPMM) recognition sites (bound, but not cleaved by the meganuclease) were co-injected with the meganuclease.

Following injection, embryos were grouped according to the criteria described above (FIG. 8B). The distribution of the transient GFP expression in F0 embryos co-injected with pαact-GFPDM or pαact-GFPMM and the meganuclease was similar to that obtained in experiments involving the injection of the pαact-GFPM2 construct with no enzyme. Therefore, the meganuclease in ovo linearization is the key process that improves transient expression in the injected one cell-stage fish embryos.

Generation of Germline-Transmitting Fish Using Meganucleases

GFP muscular expression persisted in some adults resulting from the injection experiments. An important point was therefore to investigate if and how the transgene was transmitted to the next generation, and, in particular, whether there was any correlation between levels of expression in adult muscles and the frequency of germline transmission.

In a first screen on 30 injected adults, those exhibiting no GFP expression in muscles all turned out to be negative for germline transgene transmission. Thus, adult GFP-negative fish were a priori considered as negative, and subsequently discarded from the F0 mating procedures. The observation of GFP expression in adult F0 thus greatly simplified the screen for transmitting fish.

To investigate the effects of meganuclease on the frequency of appearance of germline transmitting founders, injected fish were raised to sexual maturity and mated to wild-type partners. The level of muscular fluorescence in their three-day-old progeny was then scored as described above.

As expected, founder fish resulting from the injection without the meganuclease had mosaic germlines, and, in most lines, rates of F1 inheritance (as assayed by GFP expression) was dramatically low (transmission to only a few percents of the siblings). In a few lines (with high copy number insertions; see below) the transgene was transmitted at a moderate rate (30 to 50 percents).

In sharp contrast, the frequency of germline transmission for founders co-injected with the circular plasmid and the meganuclease was boosted to 50% in most lines (FIG. 2A), corresponding to a 5- to 15-fold increase in the mean frequency of positive embryos in the progeny.

Further Southern analysis confirmed that single integrations at a low copy number occurred in most cases.

DNA was first digested with EcoRI or XhoI, enzymes that does not cut or cuts once, respectively, into the plasmid construct (not shown). All the animals analyzed contained a single fragment of large size which hybridizes with the insert probe, suggestive of a single integration event. We cannot exclude, however, the existence of several such events, because BamHI or XbaI digestions yielded multiple junction fragments. With BamHI digestion, two (1 and 2 kb) fragments hybridising with a probe corresponding to the insert were observed, in which DNAs from fish injected with the meganuclease were loaded. These fragments corresponded respectively to the GFP/pA and to the downstream region of the actin promoter (3'□p). The presence of a 4.8 kb band, diagnostic of the upstream region of the promoter linked with the plasmid sequence (5'□p+pBluSK) suggested that some transgenes were integrated as direct tandem repeats including the plasmid. This type of integration is expected to occur if only one of the two I-SceI recognition site is cut and the insert readily integrated (with no further cut).

Discussion

This example reports on a meganuclease-mediated technology which leads to spectacular improvements in fish transgenesis at several levels.

First, the transitory expression (in F0) of an injected DNA construct is improved, due to a large increase in the number of expressing cells. Thus, mosaic expression of the reporter gene in injected embryos is greatly diminished, partly overcoming one of the main pitfalls of transgenesis in fish. This result opens the way, for example, to easier and more reliable analysis of promoter constructs in fish species, a task that often involves their preliminary transient introduction by microinjection.

Second, meganuclease-mediated technology significantly increases the rates of germline transmission in fish. Moreover, with the muscle specific promoter used, there was a good correlation between the maintenance of the reporter expression in adult injected fish and the ability to produce transgenic descendants. Therefore, the tools presented in this example greatly simplify the much time-consuming task of selecting the F0 individuals able to found a transgenic family.

Third and maybe most striking, the rate of transmission in each transmitting family was dramatically boosted in these experiments. In practice, that means that large F1 families can generated from a reasonable number of eggs. Importantly, the transmition rate of 50% observed in most crosses between transmitting F0 and wild type fish strongly suggests that a single insertion event occurred in a non-mosaic way in F0.

The control experiments allow us to propose that in vivo linearisation is instrumental in the increase of the integration rates, albeit not necessarily the only factor. For example, a nuclear targeting effect of the I-SceI enzyme may be at play in these experiments. We propose that, in a first step, the absence of free DNA ends in the circular plasmid reduces the rate of cytoplasmic degradation of the injected DNA. The late liberation of pre-integrative free ends then leads to the efficiency of integration typical of linear plasmids.

Finally, transgene integration in long concatemers, a feature often encountered in fish, never occurred in these experiments. Instead, we found that the transgene was integrated as short direct tandem repeats, a beneficial effect that is likely to be the reason for the spectacular increase in GFP expression levels.

This kind of insertion was expected because, in the plasmidic contruct, the two ISce-I sites were in the same orientation. Southern blot data also suggest that integration of similar tandemly repeated elements occurred and comprised some plasmid sequences. This indicates that these tandems are composed of several plasmids cut at only one site. Since, in vitro, ISce-I cuts at a similar kinetic at both its sites, one possible explanation for that phenomenon is that I-SceI enzyme amount was limiting with respect to DNA concentration, and that integration occurred concomitantly with the first cut.

To further improve the quality of integration, it can be proposed to change the orientations of I-SceI sites.

Applications of this technique are numerous, first of all in several fish species but also more generally. For example, it paves the route to more sophisticated experiments such as knock-out experiments by DNA injection in early embryos or oocytes.

Example 4

In ovo Linearization by the I-SceI Meganuclease in Mice

In order to improve transgenesis efficiency, we developed a novel method based on the in ovo linearization of a supercoiled plasmid by meganuclases.

Plasmid constructs have been designed to bear one or two recognition/cleaving sites for meganucleases flanking the desired transgene to be integrated. Meganuclease source was provided either by purified proteins or by in ovo production from a meganuclease-expressing vector. Improvement of transgenesis (quantitative and qualitative) was compared with experiments of "classical" transgenesis (i.e.: injection of a prelinearized and purified transgene fragment). Negative control was performed using the same supercoil preparation of transgene DNA, free of any meganuclease source.

In ovo Linearization Mediated by I-SceI Expressing Vector

Injections were performed at the one-cell stage in male pronuclei from B6SJL mouse eggs. The I-SceI expression vector was checked in ovo by microinjecting the pI-SceI/EGFP plasmid at the one-cell stage in male pronuclei from B6SJL mouse eggs. EGFP fluorescence was already vizualized at the 2-cell stage in injected embryos on an inverted microscope with EGFP filters. Due to the nature of the construct bearing an IRES in between the two I-SceI and EGFP ORFs, it assured us in about 95% of cases that when EGFP fluorescence is vizualized, I-SceI is coordinately produced. Megafluo and pI-SceI/EGFP plasmids were coinjected at five hundred copies/pl. Injected eggs were transferred in B6CBA foster female mouse. Birth was checked, still-born animals were recovered and their DNA extracted in order to be genotyped for a putative integration of the injected transgene. New-born mice were typed at 3 weeks by cutting a small piece of tail. Then, DNA extraction was performed, followed with genotyping by PCR and/or Southern experiments. From this experiment, 5 newborn and 2 still-born were recovered. Following DNA extraction, DNA recovery was checked on agarose gel. In order to check the quality of the genomic DNA extracted, a PCR amplifying a 494 bp sub-fragment of the β-globin gene was performed. All the DNA samples seemed qualitatively correct as the expected PCR β-globin product was visualized from all DNA samples tested. In order to test for the integration of the transgene, a PCR amplifying a 484 bp of the reporter gene (DSRed1-E5) was performed. Among the 5 three-weeks old mice progeny and the 2 still-born, 2 (number 1 and 25) and 1 (number A) of them were transgenic, respectively. All together, these results showed that 40% of progeny were transgenic when considering alive animals and 43% when considering altogether alive and still born injected mice.

Usually, when a coinjection of plasmid is performed in mouse one-cell stage eggs, cointegration of both plasmid is detected in injected animals and often at the same location. In order to test for the integration of the I-SceI expressing vector (pI-SceI/EGFP), a PCR amplifying a sub-fragment of this plasmid was performed as well. All the animals recovered (whether the transgenic ones for Megafluo and the non-transgenic) were negative for the presence of the I-SceI expressing vector.

In order to test for transmission of transgene to F1 progeny, transgenic animals 1 and 25 were backcrossed with B6SJL uninjected animals. Among the 13 F1 and the 54 F1 animals derived from female 1 and male 25, respectively, only one F1 animal for each back-cross was transgenic as attested by Southern Blot experiments using a probe hybridizing to the promoter pGas 5. These results demonstrated that a transgenic animals obtained by meganuclease mediated transgenesis were fertile and can transmit the transgene to their progeny. The numbers indicated a transmission rate ranging from 2 to 8% and suggested that founders were mosaic for the integration. This result was not surprising as the production of I-SceI from its corresponding expressing vectors is not suppose to start before the 2-cell-stage in mice eggs when zygotic transcription starts and CMV promoter starts to be active in mouse eggs.

In ovo Linearization Mediated by I-SceI Purified Protein

Protocol was equivalent in this experiment except that I-SceI was provided as a purified protein at a 1:5 DNA/protein ratio. 750 copies of Megafluo supercoiled plasmid was coinjected with I-SceI purified protein (18 μM). Injected eggs were transferred in B6CBA foster female mouse. Among nine new-born mice, two of them were transgenic as detected by Southern Blot analysis using either a probe corresponding to the Gas5 promoter or the plasmid backbone sequences. This result showed transgenic animals have been produced in this experiment by this method with a yield of 22%.

"Classical Transgenesis"

The same plasmid construct, Megafluo, was used in a classical protocol for mice transgenesis, i.e., injection of a prelinearized transgene. Two types of experiments were performed, one using NdeI subfragment of 1796 bp and the other using I-SceI subfragment of 1824 bp, both subfragments bearing the promoter Gas5 and the reporter fluorecent gene. Two series of injection were performed for the I-SceI fragment. The first one corresponding to the injection of 500 copies/pI of the DNA fragment has leaded to the birth of 2 mice who were negative by Red5 PCR. The second one corresponding to the injection of 750 copies/pI of the I-Sce fragment has led to the birth of 8 mice negative for the integration. The injection of 750 copies/pI of the NdeI fragment has led to the birth of 8. Among the 8 newborn, only one was transgenic (number 18). On this experiment, the number of transgenic was 12.5%. On the three experiments, 1 transgenic out of 18 born animals drop the number to 5.5% of transgenic animals obtained when using the same DNA sequence when compared to numbers obtained from meganuclease mediated transgenesis. Transmission to F1 from the transgenic male 18 was tested by crossing this male with B6SJL females. Among the 25 F1 animals, 1 out of 6 and 3 out of 19 obtained were transgenic as detected on a Southern Blot analysis using a promoter probe. These result indicated that transmission using <<classical transgenesis>> is about 16%.

Control Experiments

Integration of 750 copies/pI of the supercoiled Megafluo plasmid by itself was also checked. Two independent experiments were performed. 10 and 11 mice are obtained, respectively. Using both PCR and Southern Blot analysis in order to genotype the mice, no transgenic animal was detected.

In ovo Linearization Mediated by PI-SceI Purified Protein

In order to test the efficiency of meganuclease mediated transgenesis by an other meganuclease, we performed experiments using a purified PI-SceI protein. The transgenic construct, PIFFLago, is described in. The Gas5 promoter leading the expression of the reporter gene LagoZ (a CPG-free LacZ sequence) are flanked by two PI-SceI recognition/cleaving sites on the same orientation separating the backbone sequences of the vector. A single I-SceI site is present in between the promoter and the reporter gene.

Coinjection of 750 copies/pI of PIFFLAgo with purified PI-SceI protein at a target DNA/protein ratio of 1:25 was performed. Following transfer of the injected-eggs, foster mother was sacrified at day 12 of gestation and injected embryos were genotyped both by PCR (Lago) and Southern Blot analysis with a probe corresponding to the reporter gene sequence. Among the 10 embryos genotyped, 3 of them were transgenic. A 7 kb fragment was detected in the genomic DNA of those embryos by the Lago probe corresponding to a tandem inverted repeat intagration. This result showed that PI-SceI mediated transgensis efficiency was about 30%.

Using the same transgenic construct, I-SceI mediated transgenesis was tested by coinjecting PIFFLago at 750 copies/pI with a 1:169 I-SceI DNA target/protein Detailed Protocol for Meganuclease Mediated Transgenesis in Mice Sample Preparation for Injections Plasmid DNA (supercoiled) solutions are produced in Qiagen Endo-free columns. After precipitation, plasmids were then resuspended at the desired concentration in Brinster buffer, 10 mM TRIS, 0.25 mM EDTA. The I-SceI stock solution contained 150 µg/ml (10 units/µl) in 25 mM HEPES, pH 8, 5% glycerol. The table 3 indicates quantities of I-SceI for a series of protein:DNA ratio.

TABLE 3

| Plasmid solution | I-SceI volume (from stock at 150 µg/ml) | X buffer (to adjust the glycerol conentration to 1%) | Final volume of sample; with 500 plasmid copies per pl | Ratio protein:DNA |
|---|---|---|---|---|
| 10 µl | 0.12 µl | 9.9 µl | 20 µl | 1:1 |
| 10 µl | 0.6 µl | 9.4 µl | 20 µl | 5:1 |
| 10 µl | 1.2 µl | 8.8 µl | 20 µl | 10:1 |

Samples for injections should be prepared considering that glycerol was present in the I-SceI stock solution. Depending on the amount of I-SceI solution used, some amount of glycerol-containing solution (X buffer) should be added to have in every case a unique, constant final glycerol concentration. For injections, we used samples at 1% glycerol and a protein:DNA ratio of 5:1.

(500 copies of plasmids is equivalent to $3.01 \cdot 10^{-20}$ mol. I-SceI is 29.3 KDa)

A similar protocol was used for transgenesis mediated by PI-SceI, MM 51 kDa. On the basis of the condition of activity of PI-SceI, a stock solution of 1.15 mg/ml of PI-SceI containing 20% glycerol was prepared. Two final DNA/Ratio for injections were used: 50×(307.3 µg/ml of PI-SceI in 5.35% glycerol and 7 mM HEPES) and 94×(307.3 µg/ml of PI-SceI in 6.25% glycerol) They were prepared from dilutions of the PI-SceI stock solution in dilution buffer.

Dilution buffer:

25 mM HEPES, 5% glycerol, pH 8 at 25° C.

I-SceI-Mediated Transgenesis

The same supercoiled construction was injected either with an-expressing meganuclease vector or with the purified protein. As well, the pre-linearized and purified in vitro form of the same transgene was used to compare "classical transgenesis" with meganuclease mediated transgenesis.

Supercoil Plasmid Preparation:

Production of plasmid was performed using QIAgen Endo-free kit (QIAGEN). Recovered DNA was precipitated with NaAcetate, washed with Ethanol 70% and resuspended in Brinster buffer (10 mM TRIS-0.25 mM EDTA) at the desired concentration for injection.

Linearized Transgene Preparation:

1. Megafluo was digested to liberate transgene from plasmid vector sequences. Two different enzymes were used for that purpose: NdeI or I-SceI enzymes leading to 1796 bp and 1824 bp, respectively.

2. Restriction digest products were separated on agarose gel using 0.8% TAE.

3. Gel was placed on transilluminator and the desired band was cut out and then purified with QIAquick gel extraction kit (QIAGEN).

4. Following DNA elution in Tris (pH 7.6), DNA was precipitated, washed with Ethanol 70% and resuspended in Brinster buffer Tampon Brinster at a concentration of 500 copies/pI.

5. DNA was conserved at −20 degrees Centigrade.

Recovery of One-Cell Stage Mouse Eggs a) Superovulation:

intra-peritoneal injection of 3-weeks-old B6SJL females with PMS (folligon from Intervet) at 5 Ul/mouse, 3 days prior injection intra-peritoneal injection of 3-weeks-old B6SJL females with HCG (Chorulon from Intervet) at 5 Ul/mouse, one day prior injection and cross them with B6SJL males Cross foster B6CBA females with B6CBA vasectomized males.

b) Oocytes recovery:

Sacrifice B6SJL plugged B6SJL females, recover oviducts and piece them in PBI medium Separate oocytes in 100 µl of Hyaluronidase at 0.5 mg/ml by cutting the ampulae with forceps for 2'

Rince eggs in PBI

Transfer eggs in Whitten covered with siliconized oil and keep them at 37° C., 5% $CO_2$.

c) Egg injections:

fertilized eggs were microinjected in PBI using an Eppendorf microinjector (Femtojet 5247) with micromanipulators (transferman NK2 5188) on a Nikon inverted microscope (TE2000-U) using contention and injection capillaries (GC 100-10 and GC 100F-10 from Phymep)

d) Injected eggs transfer into foster females:

Anesthetized B6CBA females by intra-peritoneal injection of Avertin at 150 µg/ml with 400 µl/mouse Transfer injected eggs into dissected oviducts Genomic DNA Extraction 1) Add 750 µL of tail buffer and 40 µL of Proteinase K per 1 cm tail or 500 µL of tail buffer and 30 µL of Proteinase K per embryo membranes
2) Incubate at 56° C. overnight
3) Mix 5' on Eppendorf mixer
4) Add 250 µL of saturated NaCl (≈6M) per tail or 170 µL saturated NaCl (≈6M) per embryo membrane
5) Mix 5' on Eppendorf mixer
6) Centrifuge 10' at 13000 rpm
7) Collect 750 µL of supernatant in a new eppendorf tube per tail or 500 µL of supernatant per embryo membrane
8) Add 500 µL of Isopropanol per tail or 350 pL of Isopropanol per embryo membrane
9) Mix 2' on Eppendorf mixer
10) Centrifuge 1' at 13000 rpm
11) Wash pellet twice with 500 µL of EtOH 70% at RT Genotyping Transgenic Mice by Southern Blot Experiments a) Labelling of 1 µg of purified plasmidic DNA sequences o/n using the Dig-labelling kit from Roche. Probes were purified on G-50 sephadex. Quantification of probe was checked on a dot blot reaction with the Dig-control from the Roche kit.
b) From 1 to 7 µg of genomic DNA were digested o/n with EcoRI restriction enzyme (NEB)
c) Digested DNA were loaded on 0.8% agarose TAE gels
d) Gels were denatured for 30' in denaturating solution (NaOH (0.5M)+NaCl (1.5M)) then neutralized in neutralizing solution (Tris (pH 7.4, 0.5M)+NaCl (1.5M))
e) DNA transfer was made by capillarity in 10×SSC o/n on a nylon Hybond-N+ membrane (Amersham)
f) DNA was fixed on membrane by UV-crosslinking (Stratalinker from Stratagene) and bake for 2 h in a 80° c. oven
g) Membranes were prehybridized in hybridization buffer for an hour at 68° c. in a rotating oven
h) Hybridization was performed in hybridization buffer with a pre-denatured Dig-labelled probe (10 ng/ml) o/n at 68° c. in a rotating oven
i) Two washes 5' at RT with a pre-heated washing solution on a rotating plateform
j) One wash 5' at RT in Buffer I (1×)/0.3% tween k) Blocking of the membranes in Blocking solution for 30'in sealed plastic bags rotated at 250 rpm
l) Incubation of the Anti-Digoxigenin-Ap Fab fragments (Roche) at 0.0375 U/ml for 30' in blocking solution
m) Two washes in Buffer I (1×)/0.3% tween of 30' each
n) 5' in revelation buffer (Buffer III)
o) Revelation of membranes with chemioluminescent substrate CDP-Star from Roche Buffer Compositions:

Hybridization buffer: 0.5M NaPi, 7% SDS, 1 mM EDTA

Washing solution: 40 mM NaPi, 1% SDS

Buffer I (10×): 1M Maleic acid, 1.5M NaCl, pH 7.5

Blocking solution: Blocking reagent (Roche) at 10% w/v in buffer I

Buffer III (1×): Per liter: 100 mM Tris (pH 9.5), 100 mM NaCl, 50 mM MgCl2

Genotyping Transgenic Mice by PCR

PCR Reactions 100 ng of genomic DNA or 1 ng of plasmid DNA

1 µM of each primer

RED Taq Ready mix (Sigma)

DMSO from 5 to 10% depending on the pripmer used (see PCR conditions)

Qsp with autoclaved water to 10 µl

Overlay with mineral oil and place into thermal cycler.

PCR conditions:

Denaturation 3' at 94° c., 1 cycle

Denaturation 20" at 94° c.

Annealing 30" at variable temperature depending on the primers Tm

Amplification 20" at 72° c.

Final round of amplification at 72° c. for 3'35 cycles

PCR products are analyzed on 2.5% TAE agarose gel

β-globin PCR

10% DMSO, annealing at 51° c.

Oligonucleotides used for the mouse β-globin gene PCR amplification leading to the amplification of a 494 bp fragment Red PCR amplification 10% DMSO, annealing at 55° c.

Oligonucleotides used for the reporter PCR amplification of megafluo sequence leading to the amplification of a 484 bp fragment I-SceI PCR amplification 10% DMSO, annealing at 55° c.

Oligonucleotides used for the PCR amplification of a sub-fragment of the pI-SceI/EGFP sequences leading to the amplification of a 400 bp fragment Lago PCR amplification 5% DMSO, annealing at 51° c.

Oligonucleotides used for the reporter PCR amplification of PIFFLago sequence leading to the amplification of a 370 bp fragment PCR controls:

Control of contamination: identical PCR reaction except without DNA but water only (C) Positive control: B6SJL mouse DNA (wt) to ensure that the DNA sample is "amplifiable" with the use of primers for mouse beta globin demonstrating that a single copy gene can be amplified with the genomic DNAs to be genotyped.

Positive/negative supercoiled plasmid DNA were systematically used as controls in all PCR experiments.

The invention claimed is:

1. A method for randomly integrating a polynucleotide into a genome of an isolated host, said method comprising:
   a) introducing into said host cell a vector having no free 5' and 3' ends and comprising said polynucleotide, said vector comprising at least one cleavage site for meganuclease, wherein less than 5 copies of said at least one cleavage site are present in the host cell genome;
   b) causing cleavage of said at least one meganuclease cleavage site in said host cell by said meganuclease, said meganuclease being either introduced into said host cell or expressed by said host cell from a vector comprising a nucleic acid encoding said meganuclease, thereby creating or releasing said polynucleotide in a linear form having free 5' and 3' ends from said vector in said host cell; and, c) maintaining the host cell under conditions and for a period of time sufficient to cause the random integration of said created or released polynucleotide into said host cell genome.

2. The method according to claim 1 wherein said meganuclease has been introduced into said host cell.

3. The method according to claim 1, wherein said meganuclease cleavage site is not found in the host cell genome.

4. The method according to any one of claims 1–2 wherein said polynucleotide is flanked by at least one meganuclease cleavage site.

5. The method according to claim 4 wherein said polynucleotide is flanked by two meganuclease cleavage sites.

6. The method according to claim 1, wherein said meganuclease is selected from the group consisting of I-Ceu I, I-Cre I, I-Chu I, I-Csm I, I-Dmo II-Pan I, I-Sce I, I-Sce II, I-Sce III, I-Sce IV, F-Sce I, F-Sce II, PI-Aae I, PI-Ape I, PI-Ceu I, PI-Cir I, PI-Ctr I, PI-Dra I, PI-Mav I, PI-MfI I, PI-Mgo I, PI-Mja I, PI-Mka I, PI-Mle I, PI-Mtu I, PI-MtuH I, PI-Pab III, PI-Pfu I, PI-Pho I, PI-Pko I, PI-Psp I, PI-Rma I, PI-Sce I, PI-Ssp I, PI-Tfu I, PI-Tfu II, PI-Tli I, PI-Tli II, PI-Tsp I, PI-Tsp II, PI-Bsp I, PI-Mch I, PI-Mfa I, PI-Mga I, PI-Mga II, PI-Min I, PI-Mma I, PI-Msh I, PI-Msm II, PI-Mth I, PI-Tag I, PI-Thy II, I-Ncr I, I-Ncr II, I-Pan II, I-Tev I, I-Ppo I, I-Dir I, I-Hmu I, I-Hmu II, I-Tev II, I-Tev III, F-Sce II (HO), F-Suv I, F-Tev I, and F-Tev II.

7. The method according to claim 6, wherein said meganuclease is selected from the group consisting of I-Ceu I, I-Cre I, I-Sce I.

8. The method according to claim 1, wherein said meganuclease is synthetic.

9. The method according to claim 1, wherein said polynucleotide is unable to undergo homologous recombination with the host cell genome.

10. The method according to claim 1, wherein said vector is a plasmid.

11. The method according to claim 1, wherein said host cell is selected from the group consisting of a stem cell, a somatic cell, a gamete, a blastomere, and an egg.

12. The method according to claim 11, wherein said host cell is a stem cell.

13. The method according to claim 11, wherein said host cell is a somatic cell.

14. The method according to claim 11, wherein said host cell is an egg.

15. The method according to claim 1, wherein said polynucleotide sequence is a sequence encoding a polypeptide or an antisense, a regulatory sequence, or a recognition sequence for a molecule.

16. The method according to claim 11 wherein said host cell stems from a fish, a bird a non-human mammal, an insect, an amphibian, or a reptile.

17. The method according to claim 16 wherein said host cell stems from a medaka, a zebrafish, a sticklebass, an astyanax, a mouse, a chicken, a xenopus, a sheep, a cow, or a rabbit.

18. A method for producing a non-human transgenic mouse comprising:
a) isolating mouse embryonic stem cells;
b) randomly integrating a polynucleotide into the genome of said isolated embryonic stem cells by the method of claim 1;
c) producing a chimeric embryo by injecting the embryonic stem cells obtained by step b) into an embryo;
d) implanting into a surrogate mother the chimeric embryo produced by step c), and allowing production of chimeric offspring, and
e) mating the chimeric offspring to obtain transgenic animals comprising the integrated polynucleotide.

19. A method for producing a non-human transgenic animal, wherein fertilized eggs are transfected by the method according to claim 1, the fertilized eggs are reimplanted in a surrogate mother, and a non-human transgenic animal is obtained at the end of gestation.

20. A method for producing a non-human transgenic animal, wherein fertilized eggs are transfected by the method according to claim 1, the eggs are incubated in conditions appropriate for developing said transgenic animal.

21. An ex vivo method for randomly integrating a polynucleotide into a host cell genome, said method comprising:
a) introducing into said host cell a vector having no free 5' and 3' ends and comprising said polynucleotide, said vector comprising at least one cleavage site for an endonuclease having a recognition site of at least 15 nucleotides, wherein less than 5 copies of said at least one cleavage site are present in the host cell genome;
b) causing cleavage of said at least one endonuclease cleavage site by said endonuclease in said host cell, said endonuclease being either introduced into said host cell or expressed by said host cell from a vector comprising a nucleic acid encoding said endonuclease, thereby creating or releasing said polynucleotide in a linear form having free 5' and 3' ends from said vector in said host cell; and,
c) maintaining the host cell under conditions and for a period of time sufficient to cause the random integration of said created or released polynucleotide into said host cell genome.

22. The method according to claim 21, wherein said cleavage site is not found in the host cell genome.

23. The method according to claim 21, wherein said polynucleotide is flanked by at least one cleavage site.

24. The method according to claim 23, wherein said polynucleotide is flanked by two cleavage sites.

25. The method according to claim 21, wherein said endonuclease is a meganuclease.

26. The method according to claim 25, wherein said meganuclease is selected from the group consisting of I-Ceu I, I-Cre I, I-Chu I, I-Csm I, I-Dmo I, I-Pan I, I-Sce I, I-Sce II, I-Sce III, I-Sce IV, F-Sce I, F-Sce II, PI-Aae I, PI-Ape I, PI-Ceu I, PI-Cir I, PI-Ctr I, PI-Dra I, PI-Mav I, PI-MfI I, PI-Mgo I, PI-Mja I, PI-Mka I, PI-Mle I, PI-Mtu I, PI-MtuH I, PI-Pab III, PI-Pfu I, PI-Pho I, PI-Pko I, PI-Psp I, PI-Rma I, PI-Sce I, PI-Ssp I, PI-Tfu I, PI-Tfu II, PI-Tli I, PI-Tli II, PI-Tsp I, PI-Tsp II, PI-Bsp I, PI-Mch I, PI-Mfa I, PI-Mga I, PI-Mga II, PI-Min I, PI-Mma I, PI-Msh I, PI-Msm II, PI-Mth I, PI-Tag I, PI-Thy II, I-Ncr I, I-Ncr II, I-Pan II, I-Tev I, I-Ppo I, I-Dir I, I-Hmu I, I-Hmu II, I-Tev II, I-Tev III, F-Sce II (HO), F-Suv I, F-Tev I, and F-Tev II.

27. The method according to claim 26, wherein said meganuclease is selected from the group consisting of I-Ceu I, I-Cre I, I-Sce I.

28. The method according to claim 21, wherein said endonuclease is synthetic.

29. The method according to claim 21, wherein said polynucleotide is unable to undergo homologous recombination with the host cell genome.

30. The method according to claim 21, wherein said vector is a plasmid.

31. The method according to claim 21, wherein said host cell is selected from the group consisting of a stem cell, a somatic cell, a gamete, a blastomere, and an egg.

32. The method according to claim 31, wherein said host cell is a stem cell.

33. The method according to claim 31, wherein said host cell is a somatic cell.

34. The method according to claim 31, wherein said host cell is an egg.

35. The method according to claim 21, wherein said polynucleotide sequence is a sequence encoding a polypeptide or an antisense, a regulatory sequence, or a recognition sequence for a molecule.

36. The method according to claim 31, wherein said host cell stems from a fish, a bird a non-human mammal, an insect, an amphibian, or a reptile.

37. The method according to claim 16 wherein said host cell stems from a medaka, a zebrafish, a sticklebass, an astyanax, a mouse, a chicken, a xenopus, a sheep, a cow, or a rabbit.

38. A method for producing a non-human transgenic mouse comprising:
   a) isolating mouse embryonic stem cells;
   b) randomly integrating a polynucleotide into the genome of said isolated embryonic stem cells by the method of claim 21;
   c) producing a chimeric embryo by injecting the embryonic stem cells obtained by step b) into an embryo;
   d) implanting into a surrogate mother the chimeric embryo produced by step c), and allowing production of chimeric offspring, and
   e) mating the chimeric offspring to obtain transgenic animals comprising the integrated polynucleotide.

39. A method for producing a non-human transgenic animal, wherein fertilized eggs are transfected by the method according to claim 21, the fertilized eggs are reimplanted in a surrogate mother, and a non-human transgenic animal is obtained at the end of gestation.

40. A method for producing a non-human transgenic animal, wherein fertilized eggs are transfected by the method according to claim 21, the eggs are incubated in conditions appropriate for developing said transgenic animal.

* * * * *

SEQUENCE LISTING

```
<160> NUMBER OF SEQ ID NOS: 5

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence:pU3R
      sequence insert

<400> SEQUENCE: 1
attaccctgt tatccctaat gaaaga                                            26

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence:downstream
      insert of intermediate plasmid

<400> SEQUENCE: 2
tagggataac agggtaattt actttca                                           27

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence:I-SceI
      containing recognition site sequence

<400> SEQUENCE: 3
ccgctaggga taacagggta atata                                             25

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence:sequence
      with shortened recognition site

<400> SEQUENCE: 4
gggtaatata                                                              10

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:sequence
      with mutated I-SceI site

<400> SEQUENCE: 5
tagggttaac agggtaat                                                     18
```